US 11,896,303 B2

(12) United States Patent
Kumar

(10) Patent No.: US 11,896,303 B2
(45) Date of Patent: Feb. 13, 2024

(54) OPTICAL APPARATUS

(71) Applicant: Wavesense Engineering GmbH, Vienna (AT)

(72) Inventor: Abhishek Kumar, Vienna (AT)

(73) Assignee: Wavesense Engineering GmbH, Vienna (AT)

(*) Notice: Subject to any disclaimer, the term of this patent is extended or adjusted under 35 U.S.C. 154(b) by 663 days.

(21) Appl. No.: 16/630,217

(22) PCT Filed: Jul. 3, 2018

(86) PCT No.: PCT/AT2018/060133
§ 371 (c)(1),
(2) Date: Jan. 10, 2020

(87) PCT Pub. No.: WO2019/010507
PCT Pub. Date: Jan. 17, 2019

(65) Prior Publication Data
US 2020/0146545 A1  May 14, 2020

(30) Foreign Application Priority Data

Jul. 14, 2017  (AT) .................................. A295/2017

(51) Int. Cl.
*A61B 3/00* (2006.01)
*A61B 3/10* (2006.01)
(Continued)

(52) U.S. Cl.
CPC ............ *A61B 3/0025* (2013.01); *A61B 3/102* (2013.01); *A61B 3/1015* (2013.01);
(Continued)

(58) Field of Classification Search
CPC ............ G01B 9/02091; G01B 9/02044; G01B 2290/70; G01B 9/02004; G01B 11/2441;
(Continued)

(56) References Cited

U.S. PATENT DOCUMENTS 3,923,400 A   12/1975 Hardy
6,249,352 B1   6/2001 Davies et al.
(Continued)

FOREIGN PATENT DOCUMENTS

CN   103698022   4/2014
DE   3531904     3/1986
(Continued)

OTHER PUBLICATIONS

Singh, Amardeep S.G., et al., Lateral shearing digital holographic imaging of small biological specimens, Optics Express, vol. 20, No. 21, Oct. 8, 2012, p. 23617-223622.
(Continued)

*Primary Examiner* — Farhan Mahmud
(74) *Attorney, Agent, or Firm* — Simpson & Simpson, PLLC

(57) ABSTRACT

An optical apparatus is comprising an optical imaging arrangement generating either an image of the original object field or the field of the original sample at the pupil plane which consist of both amplitude and phase information. The apparatus is further comprising a digital adaptive optics arrangement with a wave front sensor and a computing unit, which is adapted to generate at least one orthogonally translated digital copy of the original sample object field at the spatial Fourier or pupil plane and to analytically calculate a wave front error based on the phase difference between the original sample wave front and its digital copy or copies.

20 Claims, 15 Drawing Sheets

(51) Int. Cl.
     *G06T 11/00* (2006.01)
     *A61B 3/12* (2006.01)
     *A61B 3/13* (2006.01)
(52) U.S. Cl.
     CPC ........... *G06T 11/008* (2013.01); *A61B 3/1225* (2013.01); *A61B 3/13* (2013.01); *G06T 2207/10101* (2013.01)
(58) Field of Classification Search
     CPC ............ G01B 9/02057; G01B 2290/45; G01B 9/0209; G01B 9/0201; G01B 9/02007; A61B 5/0066; A61B 3/102; A61B 5/7257; G01N 21/4795; G03H 1/0443; G01J 9/00
     See application file for complete search history.

(56) References Cited

U.S. PATENT DOCUMENTS

| | | |
|---|---|---|
| 2013/0057869 A1 | 3/2013 | Cotte et al. |
| 2017/0105618 A1* | 4/2017 | Schmoll ............ G02B 21/0056 |

FOREIGN PATENT DOCUMENTS

| | | |
|---|---|---|
| WO | 2003034010 | 4/2003 |
| WO | 2016173079 | 3/2016 |
| WO | 2016187675 | 12/2016 |

OTHER PUBLICATIONS

Ginner, Laurin, et al., Noniterative digital aberration correction for cellular resolution retinal optical coherence tomography in vivo, Optica, vol. 4, No. 8, Aug. 2017, pp. 924-931.
Kumar, Abhishek, et al., Subaperture correlation based digital adaptive optics for full field optical coherence tomography, Optics Express, vol. 21, No. 9, May 6, 2013, p. 10850-10866.
Liang, Junzhong, et al., Supernormal vision and high-resolution retinal imaging through adaptive optics, J. OPt. Soc. Am., vol. 14, No. 11, Nov. 1997, pp. 2884-2892.
Adie, Steven G., et al., Computational adaptive optics for broadband optical interferometric tomography of biological tissue, PNAS, vol. 109, No. 19, May 9, 2012, pp. 7175-7180.
Felberer, Franz, et al., Adaptive optics SLO/OCT for 3D imaging of human photoreceptors in vivo, Biomedical Optics Express, vol. 5, No. 2, Feb. 1, 2014, pp. 439-456.
Kumar, Abhishek, Anisotropic aberration correction using region of interest based digital adaptive optics in Fourier domain OCT, Beiomedical Optics Express, vol. 6, No. 4, Apr. 1, 2015, pp. 1124-1134.
Thurman, Samuel T., et al., Phase-error correction in digital holography, J. Opt. Soc. Am. A, vol. 25, No. 4, Apr. 2008, pp. 983-994.
Seo, Kwang-Beom, et al., Digital holographic microscopy based on a modified lateral shearing interferometer for three-dimensional visual inspection of nanoscale defects on transparent objects, Nanoscale Research Letters 9:471, 2014, pp. 1-14.
Tippie, Abbie E., et al., High-resolution synthetic-aperture digital holography with digital phase and pupil correction, Optics Express, vol. 19, No. 13, Jun. 20, 2011, pp. 12027-12038.
Katz, Ori, et al., Non-invasive single-shot imaging through scattering layers and around corners via speckle correlations, Nature Photonics, Aug. 2017, pp. 1-7.
Liu, Yuan-Zhi, et al., Computed optical interferometric tomography for high-speed volumetric cellular imaging, Biomedical Optics Express, vol. 5, No. 9, Sep. 1, 2014, pp. 2988-3000.
Babcock, H.W., The Possibility of Compensating Astronomical Seeing, Publications of the Astronomical Society of the Pacific, vol. 65, No. 386, Oct. 1953, pp. 229-236.
Booth, Martin J., et al., Adaptive aberration correction in a confocal microscope, PNAS, vol. 99, No. 9, Apr. 30, 2002, pp. 5788-5792.

Miller, Donald T., et al., Coherence gating and adaptive optics in the eye, Proceedings vol. 4956, Coherence Domain Optical Methods and Optical Coherence Tomography in Biomedicine VII, 2003, abstract provided.
Fienup, J.R., et al., Aberration correction by maximizing generalized sharpness metrics, J. Opt. Soc. Am. A, vol. 20, No. 4, Apr. 2003, pp. 609-620.
Fienup, J.R., Phase retrieval algorithms: a comparison, Applied Optics, vol. 21, No. 15, Aug. 1, 1982, pp. 2758-2769.
Brady, Gregory R., Optical wavefront measurement using phase retrieval with transverse translation diversity, Optics Express, vol. 17, No. 2, Jan. 19, 2009, pp. 624-639.
Ganesan, A.R., Universal digital speckle shearing interferometer, Applied Optics, vol. 27, No. 22, Nov. 15, 1988, pp. 4731-4734.
Brooker, Gary, et al. Optimal resolution in Fresnel incoherent correlation holographic fluorescense microscopy, Optics Express, vol. 19, No. 6, Mar. 14, 2011, pp. 5047-5062.
Hong, Jisoo, et al., Single-shot self-interference incoherent digital holography using off-axis configuration, Optics Letters, vol. 38, No. 23, Dec. 1, 2013, pp. 5196-5199.
Kim, Myung K., Adaptive optics by incoherent digital holography, Optics Letters, vol. 37, No. 13, Jul. 1, 2012, pp. 2694-2696.
Neil, M.A.A., et al., Adaptive aberration correction in a two-photon microscope, Journal of Microscopy, vol. 200, Pt 2, Nov. 2000, pp. 105-108.
Fechtig, Daniel, Full range line-field parallel swept source imaging utilizing digital refocusing, Journal of Modern Optics, vol. 62, No. 21, 2015, pp. 1801-1807.
Hardy, J.W., et al., Real-time atmospheric compensation, J. Opt. Soc. Am., vol. 67, No. 3, Mar. 1977, pp. 360-369.
Guan, Haike, et al., Analysis of Digital Lateral Shearing Interferometer, Optical Review, vol. 2, No. 6 (1995), pp. 471-475.
Poon, T.C., et al., Introduction to modern digital holography: with MATLAB, Applications in digital holography, (Cambridge University Press, 2014) pp. 151-159.
Dai, Guang-ming, Wavefront Optics for Vision Correction, Chapter 4: Ocular Wavefront Sensing and Reconstruction, SPIE Press, 2008—Abstract provided.
Schreiber, Horst, et al., Phase Shifting Interferometry, Optical Shop Testing, Third Edition, John Wiley & Sons, Inc., 2007, pp. 547-560.
Rosen, Joseph, Digital spatially incoherent Fresnel holography, Optics Letters, vol. 32, No. 8, Apr. 15, 2007, pp. 912-914.
Tyson, R.K., Principles of Adaptive Optics, Chapter 4—Adaptive Optics Systems, CRC Press, 2015, pp. 85-95.
Izatt, J.A., et al., Theory of Optical Coherence Tomography, In: Drexler W., Fujimoto J.G. (eds) Optical Coherence Tomography. Biological and Medical Physics, Biomedical Engineering. Springer, Berlin, Heidelberg (2008) pp. 47-66.
Guo, Haijun, et al., Phase information reconstruction based on digital lateral shearing approach in digital holography, Proceedings of the 29th Chinese Control Conference, Conference date Jul. 29-31, 2010; added to IEEE Xplore Sep. 20, 2010—Abstract provided.
Sherman, L., et al., Adaptive correction of depth-induced aberrations in multiphoton scanning microscopy using a deformable mirror, Journal of Microscopy, vol. 206, Pt 1, Apr. 20220, pp. 65-71.
Miller, DT, et al., Adaptive optics and the eye (super resolution OCT), Cambridge Ophthalmological Symposium, Eye (2011) 25, pp. 321-330.
Thurman, Samuel T., et al., Correction of anisoplanatic phase errors in digital holography, J. Opt. Soc. Am. A, vol. 25, No. 4, Apr. 2008, pp. 995-999.
Shemonski, N.D., et al., A computational approach to high-resolution imaging of the living human retina without hardware adaptive optics, Progress in Biomedical Optics and Imaging—Proceedings of SPIE, vol. 9307, 2015, Article No. 930710—Abstract provided.
Southwell, W.H., Wave-front estimation from wave-front slope measurements, J. Opt. Soc. Am., vol. 70, No. 8, Aug. 1980, pp. 998-1006.
Beckers, Jacques, Adaptive Optics for Astronomy: Principles, Performance, and Applications, Annu. Rev. Astron. Astrophys. 1993, 31: pp. 13-62.

(56) References Cited

OTHER PUBLICATIONS

Dean, Bruce H., et al., Diversity selection for phase-diverse phase retrieval, J. Opt. Soc. Am. A. Opt. Image Sci Vis. Aug. 2003, 20(8); 1490-504 (Abstract provided).
Paxman, R.G., et al., Optical misalignment sensing and image reconstruction using phase diversity, J. Opt. Soc. Am. A, vol. 5, No. 6, Jun. 1988, pp. 914-923.
Paxman, Richard G., et al., Joint estimation of object and aberrations by using phase diversity, J. Opt. Soc. Am. a, vol. 9, No. 7, Jul. 1992, pp. 1072-1085.
Malacara, Daniel, Optical Shop Testing, Third Edition, John Wiley & Sons, Inc., 2007.
Kumar, Abhishek, et al., Subaperture correlation based digital adaptive optics for full field optical coherence tomography, Optics Express, vol. 21, No. 9, May 6, 2013, pp. 10850-10866.
Miccio, Lisa, et al., Lateral Shear and digital holographic microscopy to check dynamic behaviour of biological cell, Proceedings of SPIE, vol. 6617, Jun. 18, 2007, p. 661706.
Kim, Byung-Mok, et al., Single-shot digital holographic microscopy with a modified lateral-shearing interferometer based on computational telecentricity, Optics Express, vol. 25, No. 6, Mar. 20, 2017, p. 6151.
International Search Report and Written Opinion for International Application PCT/AT2018/060133, dated Nov. 22, 2018; 9 pages.

* cited by examiner

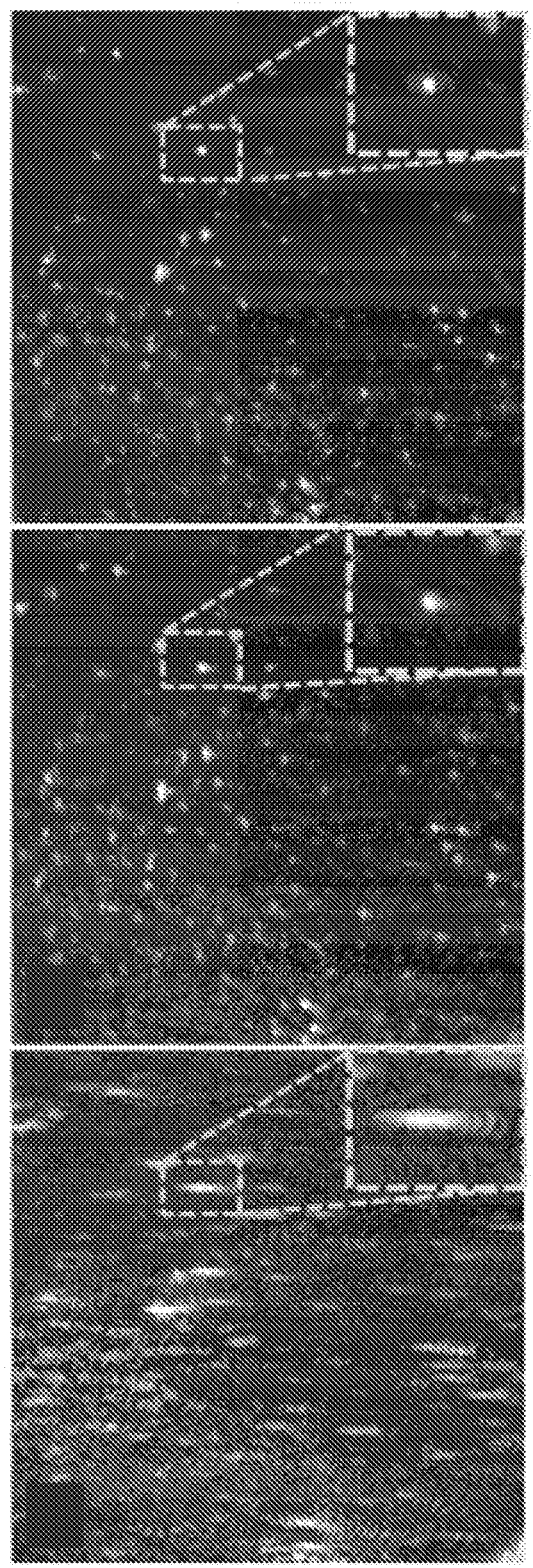
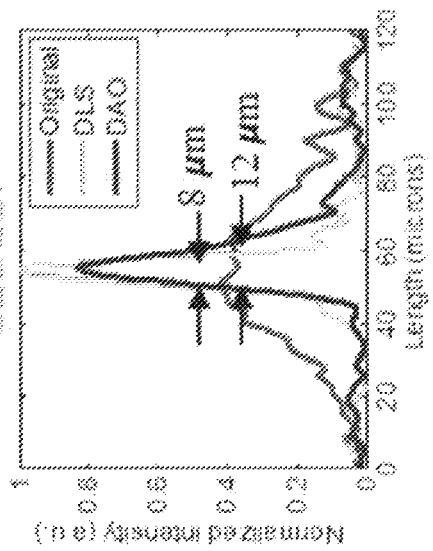
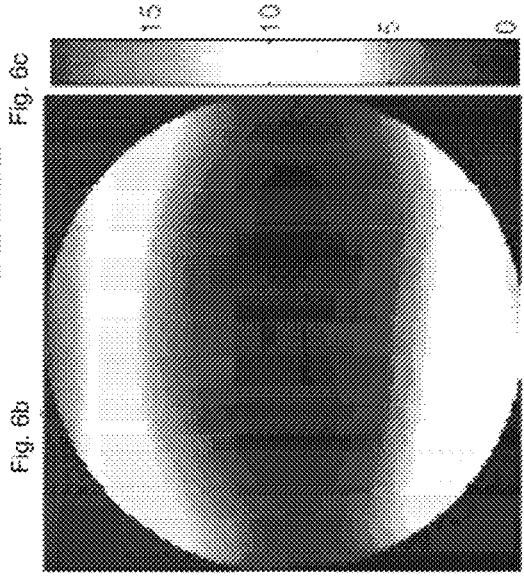
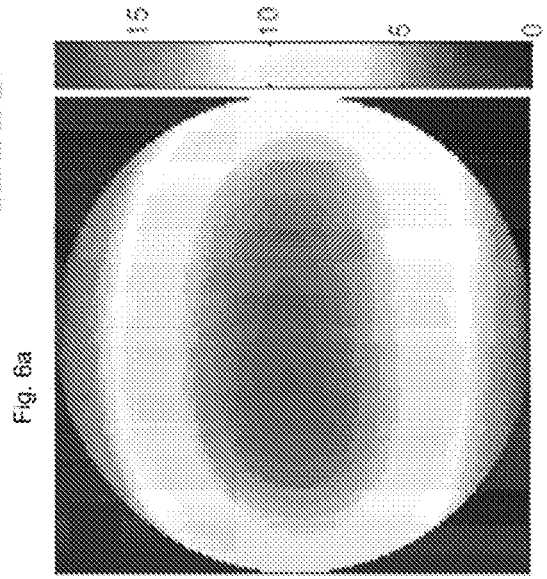
Fig. 6a  Fig. 6b  Fig. 6c  Fig. 6d  Fig. 6e  Fig. 6f

OPTICAL APPARATUS

BACKGROUND

The invention refers to an optical apparatus, comprising an optical imaging arrangement generating either an image of the original object field or the field of the original sample at the pupil plane which consist of both amplitude and phase information, further comprising a digital adaptive optics arrangement with a wave front sensor and a computing unit, according to the preamble of claim 1, as well as a computer program product, according the preamble of claim 18, for use in a digital optics arrangement using an optical apparatus.

Optical beam or wave front propagating through inhomogeneous media or imperfect optical systems suffer from aberrations which causes it to form blurred or smeared spot when focusing it using a lens. The images of an object or a scene suffer from poor resolution and quality when imaged using such an aberrated optical beam.

FIELD OF INVENTION

The presented invention provides a novel digital adaptive optics method to detect the aberrations of the wave front and also compensate or correct it to provide images of high quality and resolution.

BACKGROUND OF ART

Adaptive optics (AO) was first used in astronomy to compensate for the degrading effect of atmospheric turbulence and obtain images of celestial objects with diffraction limited resolution, as for example given in H. W. Babcock, "The Possibility of Compensating Astronomical Seeing," Publications of The Astronomical Society of The Pacific 65 (1953), J. W. Hardy, J. E. Lefebvre, and C. L. Koliopoulos, "Real-time atmospheric compensation," J. Opt. Soc. Am. 67, 360-369 (1977), or J. M. Beckers, "Adaptive Optics for Astronomy: Principles, Performance, and Applications," Annual Review of Astronomy and Astrophysics 31, 13-62 (1993).

It has been successfully translated to biomedical field such as confocal florescence microscopy, two-photon microscopy, laser eye surgery and retinal imaging with devices such as optical coherence tomography (OCT), scanning laser ophthalmoscope (SLO) and flood illumination fundus photography, as can be found in M. J. Booth, M. A. A. Neil, R. Juškaitis, and T. Wilson, "Adaptive aberration correction in a confocal microscope," Proceedings of the National Academy of Sciences 99, 5788-5792 (2002), M. Neil, R. Juškaitis, M. Booth, T. Wilson, T. Tanaka, and S. Kawata, "Adaptive aberration correction in a two-photon microscope," Journal of microscopy 200, 105-108 (2000), L. Sherman, J. Ye, O. Albert, and T. Norris, "Adaptive correction of depth-induced aberrations in multiphoton scanning microscopy using a deformable mirror," Journal of microscopy 206, 65-71 (2002), J. Liang, D. R. Williams, and D. T. Miller, "Supernormal vision and high-resolution retinal imaging through adaptive optics," J. Opt. Soc. Am. A 14, 2884-2892 (1997), D. T. Miller, J. Qu, R. S. Jonnal, and K. E. Thorn, "Coherence gating and adaptive optics in the eye," (2003), pp. 65-72, F. Felberer, J.-S. Kroisamer, B. Baumann, S. Zotter, U. Schmidt-Erfurth, C. K. Hitzenberger, and M. Pircher, "Adaptive optics SLO/OCT for 3D imaging of human photoreceptors in vivo," Biomed. Opt. Express 5, 439-456 (2014), or D. T. Miller, 0. P. Kocaoglu, Q. Wang, and S. Lee, "Adaptive optics and the eye (super resolution OCT)," Eye 25, 321-330 (2011). The combination of AO and OCT has enabled retinal layers, such as retinal nerve fiber layer (RNFL), capillaries and cone-photoreceptors, to be imaged non-invasively at the cellular level in 3-D. This has high clinical value in monitoring and early diagnosis of ocular diseases, such as retinal dystrophy, age related macular degeneration (AMD), glaucoma, diabetic retinopathy etc., which causes morphological changes in these retinal structures.

It has also found high impact application in free space optical communications, metrology and industrial inspection, manufacturing, defence and security, as explained in R. K. Tyson, *Principles of adaptive optics* (CRC press, 2015). As shown here, conventional AO consists of three main components: (1) wave front sensor (WFS), (2) wave front modulator (WFM) and (3) control system that communicates between WFS and WFM in a feedback loop. The most widely used WFS is the Shack-Hartmann wave front sensor (S-H WFS) which samples the wave front using a combination of lenslet arrays and a 2-D camera. The other types include pyramid WFS, phase diversity and curvature WFS and image sharpness sensor. WFM modify the phase of the wave front by means of reflective or transmissive techniques using either the deformable mirrors (DM) or liquid crystal spatial light modulators (LC SLM). The implementation of adaptive optics hardware in the optical system is always an engineering challenge and often makes the optical system complex and bulky in design/layout and increases the economic costs.

The U.S. Pat. No. 3,923,400 discloses a real-time wave front correction system, but uses a lateral shearing interferometer to produce displaced wave fronts. For applying phase correction some kind of deformable mirror or wave front corrector device is used. A lateral shearing interferometer for phase-different measurement of two wave fronts of constant phase is disclosed in DE3531904A1. Again, mirrors are used in a two beam lateral shearing interferometer. Also, as the title suggests, the disclosed method works only for wave fronts with constant phase. Again, a lateral shearing interferometer system with masked interference pattern is the subject of the U.S. Pat. No. 6,249,352B1. Furthermore, an additional physical mask and data processing is used to detect phase error. A two-beam lateral shearing interferometer is used in the CN103698022A. The interference of the two physically displaced beams encodes the phase error and uses a method similar to off-axis digital holography to find the phase information. The disclosed apparatus is based on automatic adaptive filtering of spectral information. All of the above-discussed systems and methods use some kind of hardware to generate a displaced copy of the original wave front. More specifically, they use some embodiment of lateral shearing interferometer.

In recent years, there is growing interest in techniques that can allow wave front error detection and correction digitally as a post processing step on a computer. Examples can be found in S. T. Thurman, and J. R. Fienup, "Phase-error correction in digital holography," J. Opt. Soc. Am. A 25, 983-994 (2008), S. T. Thurman, and J. R. Fienup, "Correction of anisoplanatic phase errors in digital holography," J. Opt. Soc. Am. A 25, 995-999 (2008), A. E. Tippie, A. Kumar, and J. R. Fienup, "High-resolution synthetic-aperture digital holography with digital phase and pupil correction," Opt. Express 19, 12027-12038 (2011), A. Kumar, W. Drexler, and R. A. Leitgeb, "Subaperture correlation based digital adaptive optics for full field optical coherence tomography," Opt. Express 21, 10850-10866 (2013), D. J. Fechtig, A. Kumar, W. Drexler, and R. A. Leitgeb, "Full range line-field parallel swept source imaging utilizing digital refocusing," Journal of Modern Optics, 1-7 (2014), S. G. Adie, B. W. Graf, A. Ahmad, P. S. Carney, and S. A. Boppart, "Computational adaptive optics for broadband optical interferometric tomography of biological tissue," Proceedings of the National Academy of Sciences (2012), A. Kumar, T. Kamali, R. Platzer, A. Unterhuber, W. Drexler, and R. A. Leitgeb, "Anisotropic aberration correction using region of interest based digital adaptive optics in Fourier domain OCT," Biomed. Opt. Express 6, 1124-1134 (2015), N. D. Shemonski, S. G. Adie, Y.-Z. Liu, F. A. South, P. S. Carney, and S. A. Boppart, "A computational approach to high-resolution imaging of the living human retina without hardware adaptive optics," (2015), pp. 930710-930710-930717, Y.-Z. Liu, N. D. Shemonski, S. G. Adie, A. Ahmad, A. J. Bower, P. S. Carney, and S. A. Boppart, "Computed optical interferometric tomography for high-speed volumetric cellular imaging," Biomed. Opt. Express 5, 2988-3000 (2014), or L. Ginner, A. Kumar, Daniel Fechtig, L. M. Wurster, M. Salas, M. Pircher, and R. A. Leitgeb, "Noniterative digital aberration correction for cellular resolution retinal optical coherence tomography in vivo," Optica 4, 924-931 (2017).

This can obviate the need for any additional AO hardware, which can allow the optical system to be more compact and cheap. Such techniques commonly referred to as digital/computational adaptive optics (D/C AO), require both amplitude and phase (i.e. complex field) information of the signal. Hence, DAO can be implemented in any holographic or interferometric system using a coherent or partially coherent light source that can provide access to phase of the signal. However, using phase retrieval techniques, complex field information of the signal can also be obtained in case of incoherent systems, where only intensity of the signal is recorded. Publications referring to this topics are i. a. J. R. Fienup, "Phase retrieval algorithms: a comparison," Appl. Opt. 21, 2758-2769 (1982), G. R. Brady, M. Guizar-Sicairos, and J. R. Fienup, "Optical wave front measurement using phase retrieval with transverse translation diversity," Opt. Express 17, 624-639 (2009), B. H. Dean, and C. W. Bowers, "Diversity selection for phase-diverse phase retrieval," JOSA A 20, 1490-1504 (2003), R. Paxman, and J. Fienup, "Optical misalignment sensing and image reconstruction using phase diversity," JOSA A 5, 914-923 (1988), R. G. Paxman, T. J. Schulz, and J. R. Fienup, "Joint estimation of object and aberrations by using phase diversity," JOSA A 9, 1072-1085 (1992), J. R. Fienup, "Phase retrieval algorithms: a personal tour [invited]," Appl. Opt. 52, 45-56 (2013), or O. Katz, P. Heidmann, M. Fink, and S. Gigan, "Non-invasive single-shot imaging through scattering layers and around corners via speckle correlations," Nature photonics 8, 784-790 (2014).

Digital Holographic (DH) systems with incoherent light sources, such as incoherent digital adaptive holographic optics (IDAHO), Fresnel incoherent correlation holography (FINCH) etc., have also been demonstrated, as explained in J. Rosen, and G. Brooker, "Digital spatially incoherent Fresnel holography," Opt. Lett. 32, 912-914 (2007), G. Brooker, N. Siegel, V. Wang, and J. Rosen, "Optimal resolution in Fresnel incoherent correlation holographic fluorescence microscopy," Opt. Express 19, 5047-5062 (2011), M. K. Kim, "Adaptive optics by incoherent digital holography," Opt. Lett. 37, 2694-2696 (2012), or J. Hong, and M. K. Kim, "Single-shot self-interference incoherent digital holography using off-axis configuration," Opt. Lett. 38, 5196-5199 (2013).

Interferometric and holographic systems come in variety of configurations. Commonly used interferometers are based on double/multiple path, open path and common path configurations with prominent examples being Michelson, Mach-Zehnder and laser Fizeau interferometer respectively, as disclosed in D. Malacara, *Optical shop testing* (John Wiley & Sons, 2007). In all these interferometer variations, phase of the wave front can be detected using phase shifting techniques that introduce time varying phase shift between the sample and the reference wave front. The relative phase between the two wave fronts is encoded in this time varying signal which can be extracted using numerical techniques. Phase shift can be introduced in a number of ways, such as: 1) by translating the reference mirror of the interferometer with a piezo-electric transducer, 2) using a moving grating or acusto-optical modulator to introduce Doppler frequency shift, 3) using a frequency domain optical delay line that consists of grating, lens and a titled mirror in the reference arm, 4) by causing optical delay using fiber stretcher. DH systems are, see T.-C. Poon, and J.-P. Liu, *Introduction to modern digital holography: with MATLAB* (Cambridge University Press, 2014), generally classified as Fresnel or Fourier holography depending on how the diffraction of object is defined in the hologram recording plane. These can be further classified as inline and off-axis holography depending on whether the object and the reference wave overlap along the same direction or with an angle respectively. For inline holography, phase of the wave front can be detected using some of the phase shifting techniques described for interferometry. In case of off-axis holography, the spatial carrier frequency introduced by the relative tilt of the reference wave front separates the complex valued object field term from its complex conjugate (twin image) and DC and auto-correlation terms in the spatial Fourier domain (FD), which can be then filtered out digitally. Since all these systems provide access to the complex field/phase information of the sample wave front, DAO has the potential of application in all such systems. DAO can also be implemented in interferometric tomographic setups such as OCT, which is described in the theory section and used for proof of principle study in the experiment presented in the manuscript.

Conventional DAO techniques, based on optimization algorithms, vary the coefficients of the phase correction function in an iterative manner until image quality or sharpness metric meets the desired criteria, what can be found in publications given above and for example also in J. R. Fienup, and J. J. Miller, "Aberration correction by maximizing generalized sharpness metrics," J. Opt. Soc. Am. A 20, 609-620 (2003). These DAO techniques are usually computationally intensive, often take long iterations and can even require manual adjustment of coefficients of Zernike polynomials representing the wave front error in order to achieve optimal performance. They are also highly dependent on the nature and quality of the image. Kumar et al. demonstrated a sub-aperture based DAO method which is the digital equivalent of SH WFS, as given in A. Kumar, W. Drexler, and R. A. Leitgeb, "Subaperture correlation based digital adaptive optics for full field optical coherence tomography," Opt. Express 21, 10850-10866 (2013). In this method, the aperture at the pupil plane or the spatial Fourier plane is digitally divided or segmented into subapertures. The images of the subapertures are then cross-correlated with the image of central subaperture, taken as reference, to detect relative shifts in the presence of any wave front aberration. The wave front is reconstructed analytically in a single step using a set of basis functions and local slope data put in a matrix formulation based on least square fit.

The US2013057869A1 discloses the use of digital image processing techniques such as inverse scattering or design of deconvolution filter function based on modelling of imaging system, using a mathematical model for the imaging system requiring a priori knowledge of the system parameters. The WO2016173079A1 discloses a digital phase shift lateral shearing interferometer, but use two expensive spatial light modulators and program it with a computer to act like a grating to produce displaced copies and then filter out all copies except one which is interfered with the original wave front. The WO2016187675A1, finally, mentions a 3-D spectral domain optical coherence tomography (OCT) apparatus utilizing a multi-wavelength optical source and an angularly variable illumination system that samples the complex field. This kind of system is only suitable for digital or numerical refocusing methods described by for instance by the paper: A. Kumar, W. Drexler, and R. A. Leitgeb, "Subaperture correlation based digital adaptive optics for full field optical coherence tomography," Opt. 30 Express 21, 10850-10866 (2013).

OBJECTS AND ADVANTAGES

The object of the present invention is therefore a novel digital adaptive optics apparatus and method to detect the aberrations of the wave front and also to compensate or correct it to provide images of high quality and resolution.

This is achieved according to the present invention by the features of the independent claim(s). Advantageous further embodiments are disclosed in the drawing figures and in the dependent claims.

SUMMARY OF THE INVENTION

According to the present invention, an optical apparatus is provided, comprising an optical imaging arrangement generating either an image of the original object field or the field of the original sample at the pupil plane which consist of both amplitude and phase information, further comprising a digital adaptive optics arrangement with a wave front sensor and a computing unit.

To solve the object given above, this apparatus is characterized in that the computing unit is adapted to generate at least one orthogonally translated digital copy of the original sample object field at the spatial Fourier or pupil plane and to automatically determine a wave front error based on the phase difference between the original sample wave front and its digital copy or copies.

Preferably, the computing unit is adapted to generate the digital copy of the original object field at the pupil plane by performing digitally a 2-D fast Fourier transformation on the image field and then shifting it by at least one pixel in orthogonal directions.

An optional feature of the present invention provides the optical apparatus designed as digital holography system, phase sensing interferometric system or interferometric tomographic system, in particular optical coherence tomography. The optical apparatus according to the present invention can also be integrated and/or used in any of the mentioned systems.

Preferably, such optical apparatus is characterized by a source of laser light or a broad band partially coherent light source, collimation optics for the light from said source, a beam splitter arrangement directing a part of the laser light to a sample arm including focusing optics and another part of the laser light to a reference arm, a scanner placed at the Fourier plane of the focusing optics, a sample carrier, preferably a three-dimensional translation stage, and a photodetector unit for detecting the recombined light from the sample arm and the reference arm after the beam splitter, said photodetector unit connected with the computing unit for digitalization and further data processing.

A preferred embodiment is characterized in that the reference arm includes an element matching the dispersion caused by the optics in the sample arm.

Another embodiment is characterized in that the reference arm includes a phase or frequency shifting device.

A still further embodiment is characterized by either imaging or collimation optics placed before the photodetection unit.

Preferred, the optical apparatus according to the invention is characterized by a pixelated phase mask, placed at a plane conjugate to the sample plane, where the beam is focused using focusing optics, and collimation or imaging optics between the phase mask and the photodetector unit.

Optionally, a swept source laser or a tuneable frequency laser is used in combination with a single element photodetector.

Another embodiment can be provided, characterized in that a broad-band light source is used in combination with a spectrometer based photodetector unit.

Said embodiment is preferably characterized in that the photodetector unit consists of a diffraction grating and a one-dimensional array of photodetectors.

The optical apparatus could also be characterized by a light source, collimation optics and a linear polarizer for the light from the light source, a reflective polarizing beam splitter followed by a quarter wave plate, a scanner and focusing optics, a sample carrier for a reflective sample, with the optical path for the light reflected back from the sample including again the quarter wave plate, a first telescope arrangement, a beam splitter after the first telescope, followed by a second telescope arrangement with a pin-hole filter placed the intermediate focal plane of the telescope for one of the split beams, and a photodetector unit for the combined beams at the back focal plane of the second telescope, said unit connected with the computing unit for digitalization and further data processing.

Preferred, such optical apparatus can be characterized in that a pixelated phase mask is placed at the intermediate focal plane of the second telescope where one of the beams is focused, with the other beam filtered by a pin-hole filter.

Such optical apparatus could also be characterized by a mirror replacing the reflective sample and a support for placing a transmissive sample at the intermediate focal plane of the first telescope. The sample/object can be any turbid media, which can be preferably optically transparent or reflective, which can include biological tissues such as skin or eye.

A further embodiment of the optical apparatus according to the present invention can be characterized in that a scanner receiving a combined collimated reference and sample beam is followed by focusing optics and is further followed by a pinhole filter arranged to overlap the focused sample beam with a spot formed by the reference beam, the scanner being adapted to translate the spots over the pinhole, and a single element photodetector unit for receiving the light passing the pin hole filter.

A still further embodiment can be provided, characterized in that a scanner receiving a combined collimated reference and sample beam is followed by focusing optics and is further followed by a pinhole filter arranged to overlap the focused sample beam with a spot formed by the reference beam, the scanner being adapted to translate the spots over the pin-hole, followed by an arrangement of collimation optics, a diffraction grating or prism, focusing optics and a one dimensional array of photodetectors to receive the light passing the pin hole filter.

Systems based on the two preceding paragraphs can be used as aberrometer, which can provide depth resolved 3-D wave front error map as light propagates through the turbid media and is imaged by the claimed system realizations.

An optical apparatus according to the invention can be designed as incoherent system including phase retrieval technique arrangements. In a preferred embodiment a white light source is used.

A preferred embodiment is characterized by a light source, followed by a linear polarizer and a non-polarizing beam-splitter, a flip polarization beam splitter which can be pivoted in and out of the light path, which beam splitter when pivoted in the path of light coming from the first non-polarization beam splitter, the sample path contains a telescope and an aperture, a quarter wave plate at 45° with respect to the optical axis, and a flip non-polarizing beam splitter, preferably with 50% power, further with a sample light path for the back-reflected light, containing the same flip non-polarizing beam splitter, two telescopes with an intermediate X-Y galvo scanner system and the above mentioned quarter wave plate, and with a reference path containing an adjustable reference mirror.

Both flipable polarization beam splitters and non-polarization beam splitters are flipped in and out at the same time. Preferred light sources are a monochromatic coherent continuous wave (CW) or pulsed laser, a frequency tuneable laser source or a broad band partially coherent light source. The reference path can optionally contain also at least one of a quarter wave plate or a dispersion compensation glass. In this configuration, the system can be used as an aberrometer, with the detection arm consisting of a collimator and a photo-detection unit.

In another configuration both the flipable polarization beam splitter and the non-polarization beam splitter are pivoted out of the light path. In this case, the illumination and detection beam path contains the two-telescope arrangement with galvo scanner placed at the focal plane. In this configuration the system can be used as imaging device.

A still further embodiment of an optical apparatus is characterized by a swept source laser as the light source, a fiber coupler splitting the light path into a sample light path and the reference light path, the reference light path containing a collimator, an adjustable reference mirror and a further collimator, the sample light path containing a collimator, three deflection mirrors and a beam splitter, further a telescope behind the beam splitter, on the opposite side of the sample location, followed by a X-Y galvo scanner, a second telescope and a further collimator, the sample light path and the reference light path combined together into a further fiber coupler, the output side of said fiber coupler connected to a dual balance detector.

The present invention comprises also a computer program product, for use in a digital optics arrangement as disclosed in the preceding paragraphs. According to the present invention, it is characterized in that it generates at least one orthogonally translated digital copy of an original object field of an optical apparatus at the spatial Fourier plane and then determines a wave front error based on the phase difference between the original wave front and its digital copy or copies, when loaded into a computing unit of the digital adaptive optics arrangement.

A preferred embodiment of such computer program product can be characterized in that it generates the digital copy of the original object field at the pupil plane by performing digitally a 2-D fast Fourier transformation on the image field and then shifts it by at least one pixel in orthogonal directions.

The apparatus according to the present invention provides a novel DAO technique, which is a digital equivalent of lateral shearing (LS) interferometry. This approach is referred to as digital lateral shearing based DAO (DLS-DAO) in the following. In conventional LS interferometry, the wave front is interfered with the physically generated duplicate and displaced copy of itself and the wave front error is estimated by analyzing the shape of the fringes of the resulting interferogram. This is disclosed in D. Malabari, Optical shop testing (John Wiley & Sons, 2007).

In the method according to the present invention, digital laterally sheared (orthogonally translated) duplicate copies of the original object field at the spatial Fourier plane is generated with the aid of a computer. Using the phase difference between the original and the digital copies, wave front error is calculated. This approach enables higher resolution, accuracy and speed as: 1) single pixel in measurement data corresponds to single phase data point, 2) digital copies are free from any artefacts/imperfections that may arise from hardware based methods and 3) it works with single shot data with significantly less computational burden compared to other DAO techniques. This method can work with digital holography (DH) or phase sensing interferometric systems. The sensitivity, dynamic range and accuracy of this method is expected to be limited by the resolution and shot noise limited performance of the DH or interferometric system. Simulation study demonstrates that this method provides measurement with higher accuracy with a speed that is an order of magnitude faster as compared to subapertures based DAO in presence of higher order aberrations. This observation is supported by experimental study conducted using a swept source optical coherence tomography (SS OCT) system, which is a kind of interferometric imaging system, and a micro-beads phantom as a sample.

The presented DAO technique is different from the conventional wave front sensor based on LS interferometer as it does not require an actual LS interferometer. It can also work with DH or any phase sensitive interferometric system where recoding is either done in the image plane or in the pupil/Fourier plane where beam is collimated. Hence, there is no need to modify the system or add additional hardware. Conventional LS interferometry measurement cannot be done in the image plane where the beam is focused. The apparatus according to the present invention can be used in both full field and point scanning system where the object under inspection contains point like guide star structures.

Instead of using complicated and expensive hardware, the duplicate laterally sheared copies of the object field at the pupil plane are generated digitally by performing a 2-D fast Fourier transformation (FFT) on the image field and shifting it by a pixel or two in orthogonal directions on a computer. Said measure provides for precise control of shift in terms of pixels and the duplicate digital copies are free from any artefacts that may be caused by optics or hardware in physical methods. Thus, it can provide measurement with higher resolution and accuracy as compared to conventional hardware based LS approach.

In comparison to SH WFS, wherein resolution and dynamic range is limited due to the physical size of the lenslet arrays, DLS-DAO can provide measurement with higher resolution and flexible dynamic range as single pixel corresponds to the single-phase data.

Unlike phase diversity and curvature WFS, DLS-DAO does not require any variable curvature mirror or translation of detector. Instead, it can work with single shot data with simple implementation which does not require any complex mathematical differential calculations.

In comparison to sharpness maximization WFS or sub-aperture based DAO technique, it has significantly reduced computational burden and also does not require any a priori system knowledge such as wavelength, numerical aperture (NA), focal length of objective lens or pixel size of the detectors etc. It is non-iterative in nature, requires less number of FFT operations and does not require any cross-correlation or differential equation solver. Hence, DLS-DAO can provide significantly higher frequency of measurement.

Further advantages, features and details of the invention can be gathered from the following specification, describing embodiments of the invention and referring to the drawing figures. The features recited in the claims and in the specification, respectively, can be essential for the invention either individually or in arbitrary combination.

The list of reference numerals is part of the disclosure. The drawing figures are described in correlation and jointly. Same reference numerals are used for same parts. Reference numerals with different indices are used for functionally identical or similar parts.

BRIEF DESCRIPTION OF THE DRAWINGS

FIG. 6 shows an original OCT enface image of a micro-beads phantom, the image obtained by subaperture-DAO and the image obtained by DLS-DAO, a phase error estimation in radians by subaperture-DAO, a phase error estimation in radians by DLS-DAO, and profile plots across the guide star before and after corrections, FIG. 14 shows the retinal imaging mode, while

DETAILED DESCRIPTION

Figure 1:
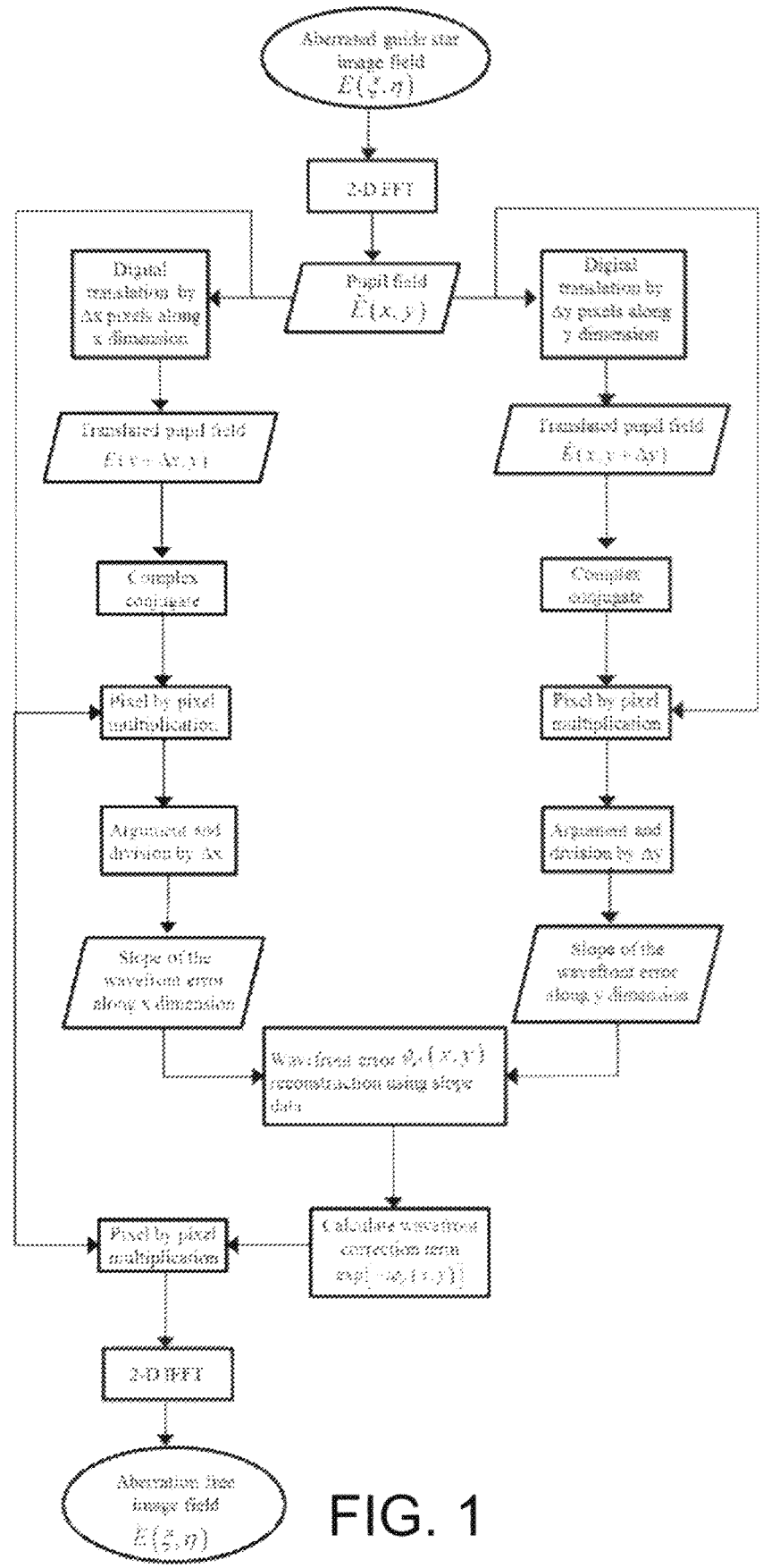
FIG. 1 shows a flowchart of the algorithm for phase error estimation and correction used in the apparatus according to the present invention.

In the following specification below, preferred embodiments and variants of the invention are explained in more detail. Individual features of the presented embodiments can be exchanged among each other or combined arbitrarily.

In interferometric imaging, the detected signal is given by $$I_d(\xi,\eta,t) = |E_o(\xi,\eta,t)|^2 + |E_R(\xi,\eta,t)|^2 + E_o(\xi,\eta,t)E_R^*(\xi,\eta,t) + E_o^*(\xi,\eta,t)E_R(\xi,\eta,t) \quad (1)$$

where $E_o$ and $E_R$ are the image of the object/sample and the reference field at the detector plane respectively, and $(\xi,\eta)$ is the coordinate of the detector plane. The complex valued signal, that contains the phase/wave front information about the object, $E_s = E_o E_R^*$ can be retrieved by using phase shifting techniques that modulates the interference signal in time t. This can be done for example by translating the reference mirror with a piezo-electric transducer, or by introducing optical frequency shift in the reference light by using a moving grating or by using an acousto-optic modulator. Another method is to introduce spatial carrier frequency by tilting the reference mirror in an off-axis configuration, which separates the complex valued signal of interest $E_s = E_o E_R^*$ from the complex conjugate term $E_s^* = E_o E_R$ in the spatial Fourier domain (FD), which can be then filtered out digitally. These methods can be used to detect phase information in a time domain (TD) OCT system, which is based on interferometric imaging with low coherence light source, and which provides depth information about the sample. In FD OCT system, the spectrum of interference signal is recorded either spatially using a broad band light source and a spectrometer, or temporally by frequency sweeping the laser source. 1-D Fast Fourier transformation (FFT) of the signal along the frequency dimension, gives the complex valued signal for each depth in the sample, as can be gathered e.g. from W. Drexler, and J. G. Fujimoto, "Optical Coherence Tomography: Technology and Applications" (2015). Since the focus of the presented research work is OCT, we assume from henceforth that we have access to the complex valued data which contains phase information corresponding to each depth of the sample. The 2-D Fourier transformation of the complex data corresponding to enface plane at a given depth can be written as $$FT_{2D}[E_s(\xi,\eta)] = \tilde{E}_s(x,y) = \tilde{E}_{ideal}(x,y)\exp[i\phi_e(x,y)] \quad (2)$$

where $E_s$ is the Fourier transformation of $E_s$, $\tilde{E}_{ideal}$ is the ideal band-limited Fourier transformation of the signal without any optical aberration, $\phi_e$ is the phase error, and (x,y) is the coordinate in the Fourier plane. We calculate the shifted version of $\tilde{E}_s$, shifted by small distance $\Delta x$ and $\Delta y$ along x and y respectively as $$\tilde{E}_s(x+\Delta x,y)=\tilde{E}_{ideal}(x+\Delta x,y)\exp[i\phi_e(x+\Delta x,y)], \text{ and} \quad (3)$$

$$\tilde{E}_s(x,y+\Delta y)=\tilde{E}_{ideal}(x,y+\Delta y)\exp[i\phi_e(x,y+\Delta y)]. \quad (4)$$

If we consider the object to be point like, then we can write $$E(\xi,\eta)=\delta(\xi,\eta)A(\xi,\eta)\exp[i\varphi((\xi,\eta)] \quad (5)$$

where $\delta(\xi,\eta)$ is the Kronecker delta function, A is the amplitude and $\varphi$ is the phase. In this case the Fourier transformation of the ideal signal is given by $$\tilde{E}_{ideal}(x,y)=\tilde{E}_{ideal}(x+\Delta x,y)=\tilde{E}_{ideal}(x,y+\Delta y)=A(0,0)\exp[i\varphi(0,0)]. \quad (6)$$

Multiplying $\tilde{E}_s(x+\Delta x,y)$ with conjugate of $\tilde{E}_s(x,y)$ on a point by point basis and using Eqs. (5)-(6) we get $$\tilde{E}_s(x+\Delta x,y)\tilde{E}_s^*(x,y)=|A(0,0)|^2 \exp\{i[\phi_e(x+\Delta x,y)-\phi_e(x,y)]\}. \quad (7)$$

Taking the argument of Eq. (7), and using the first order Taylor expansion we get $$\measuredangle[\tilde{E}_s(x+\Delta x, y)\tilde{E}_s^*(x,y)] = \left[\phi(x,y) + \Delta x \frac{\partial \phi(x,y)}{\partial x}\right] - \phi(x,y). \quad (8)$$

Hence, we can find the slope $s_x$ of the wave front error $\phi_e$ along x as $$s_x(x,y) = \frac{\partial \phi(x,y)}{\partial x} = \left(\frac{1}{\Delta x}\right)\measuredangle[\tilde{E}_s(x+\Delta x, y)\tilde{E}_s^*(x,y)]. \quad (9)$$

Similar, the slope $s_y$ of the wave front error along y is given by $$s_y(x,y) = \frac{\partial \phi(x,y)}{\partial x} = \left(\frac{1}{\Delta y}\right)\measuredangle[\tilde{E}_s(x,y+\Delta y)\tilde{E}_s^*(x,y)]. \quad (10)$$

We refer to the method of determination of slopes using Eqs. (9)-(10) as digital lateral shearing (DLS) based digital adaptive optics (DAO). Since the data is in digital format, for a pupil size of M×M pixels, we have $M^2$ samples for both $s_x$ and $s_y$. The shearing in x and y, i.e. $\Delta x$ and $\Delta y$ are also in terms of pixels. We used pixel shift of unity in our experiments to get shifted versions of $\tilde{E}_s$ along x and y. Thus, slope information can be obtained without the knowledge of any system parameters. We can represent the phase error in terms of orthogonalized Zernike polynomials as $$\phi_e(\bar{x},\bar{y}) = \sum_{i=1}^{P} a_i Z_i(\bar{x},\bar{y}) \quad (11)$$

where $(\bar{x},\bar{y})$ is the normalized the co-ordinate in the Fourier space such that the aperture lies within a circle of unit radius.

We compare the gradient of the phase error function with the calculated slope data and write the problem in the matrix form as $$S=GA \quad (12)$$

where $S=[Sx;Sy]$ with $S_x=[\bar{s}_{x,1}, \ldots, \bar{s}_{x,M^2}]^T$ and $S_y=[\bar{s}_{y,1}, \ldots, \bar{s}_{y,m^2}]^T$ as the column vectors containing normalized x and y slope components, $G=[\partial Z/\partial \bar{x}; \partial Z/\partial \bar{y}]$ is the gradient matrix with $\partial Z/\partial \bar{x}$ and $\partial Z/\partial \bar{y}$ as ($M^2 \times P$) matrices of partial derivate of Zernike polynomials $z_i(\bar{x},\bar{y})$ with respect to $\bar{x}$ and $\bar{y}$, and $A=[a_1, \ldots, a_P]^T$ is the vector containing the Zernike coefficients. We can estimate the least square solution for Eq. (11) as $$\hat{A}(G^TG^{-1})G^TS. \quad (13)$$

The phase error can be calculated once the estimate of the coefficients can be determined using Eq. (13). The method described here for wave front reconstruction using a set of basis functions and matrix formulation based on least square fit is referred to as Modal reconstruction. The basis function such as Taylor monomials or Fourier series can also be chosen instead of Zernike polynomials. The other method referred to as Zonal reconstruction involves least square fitting of wave front from the neighbouring local slopes, explained in W. H. Southwell, "Wave-front estimation from wave-front slope measurements," J. Opt. Soc. Am. 70, 998-1006 (1980) or G.-m. Dai, *Wavefront optics for vision correction* (SPIE press, 2008). The phase corrected image is obtained by first multiplying $\tilde{E}_s$ with correction factor $\exp(-i\phi_e)$ and calculating the inverse 2-D Fourier transformation. The flowchart of the algorithm for phase correction is shown in FIG. 1. In our theoretical development, we have assumed our object to be point like and in the absence of any optical aberration should ideally have a flat wave front at the Fourier plane. Any deviation from this ideally flat wave front can be detected with DLS-DAO. However, in presence of wide field object, the ideal wave front at the Fourier plane will not be flat and will contain range of frequencies. The wave front error detection using DLS-DAO will fail in that case. However, this method is still useful where focusing of light in the sample is involved, for example in point scanning OCT and adaptive optics systems. Also for scene based imaging, this method can be useful if some guide stars are present within the field of view.

To simulate the aberrated image field of a point object (or the point spread function (PSF)), first 2-D FFT of matrix of size 512×512 pixels with center pixel value of unity and zero elsewhere is calculated. The calculated Fourier data is band-limited by multiplying it with a circular pupil of radius 128 pixels with pixel value of unity inside the radius and zero elsewhere. To introduce the wave front error, the resultant data is multiplied with phase error factor $\exp[i\phi_e(\bar{x},\bar{y})]$ where $\phi_e(\bar{x},\bar{y})$ is calculated using Eq. (11). The coefficients of the Zernike polynomials of up to say $P^{th}$ order are selected from normally distributed random number, and the overall phase is then scaled to get the desired peak to valley (P-V). Finally, 2-D IFFT of the result is calculated to get the aberrated PSF.

Figure 2:
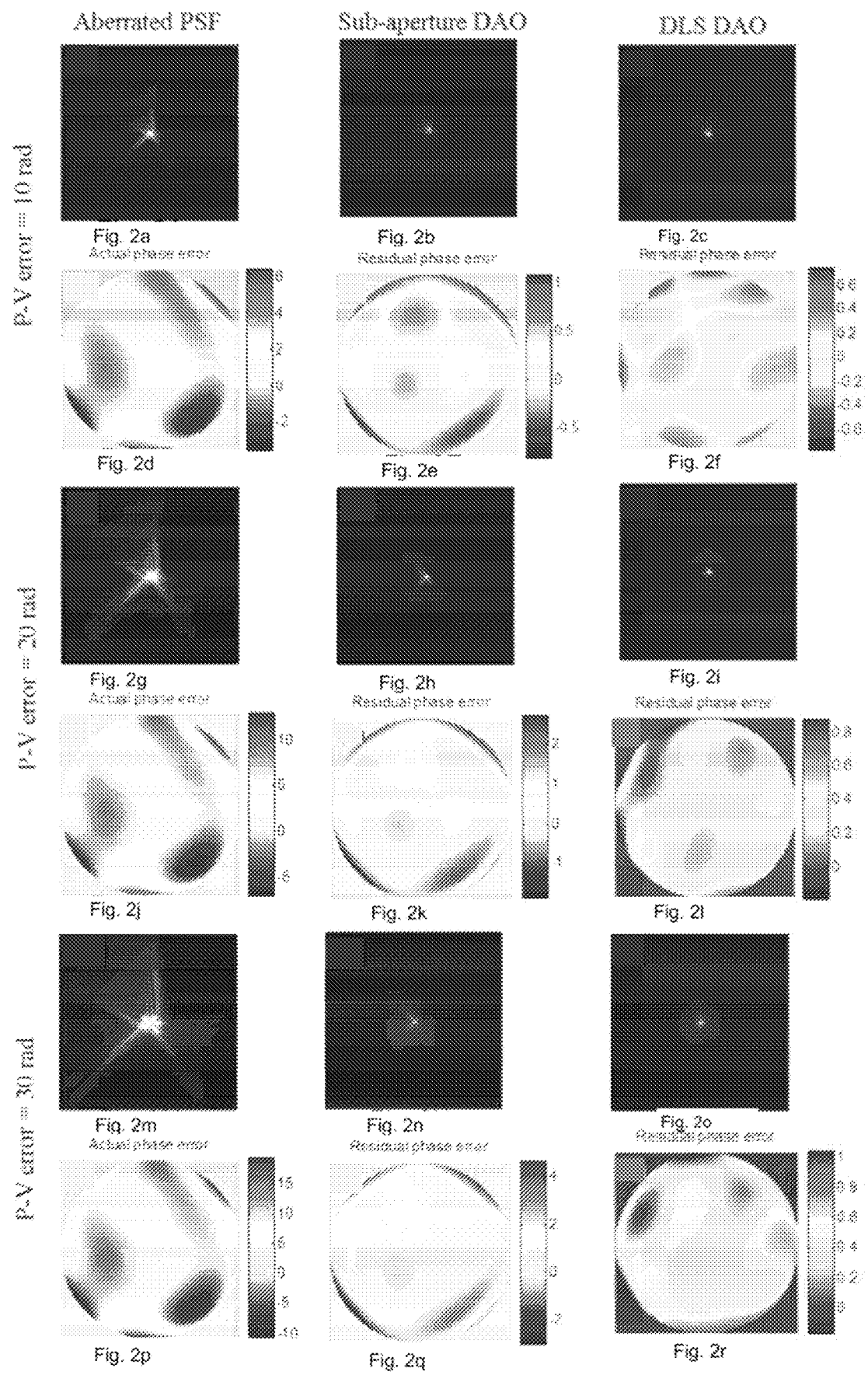
FIGS. 2a to 2r show point spread functions (PSFs) explaining the effect of the present invention.
Figure 3:
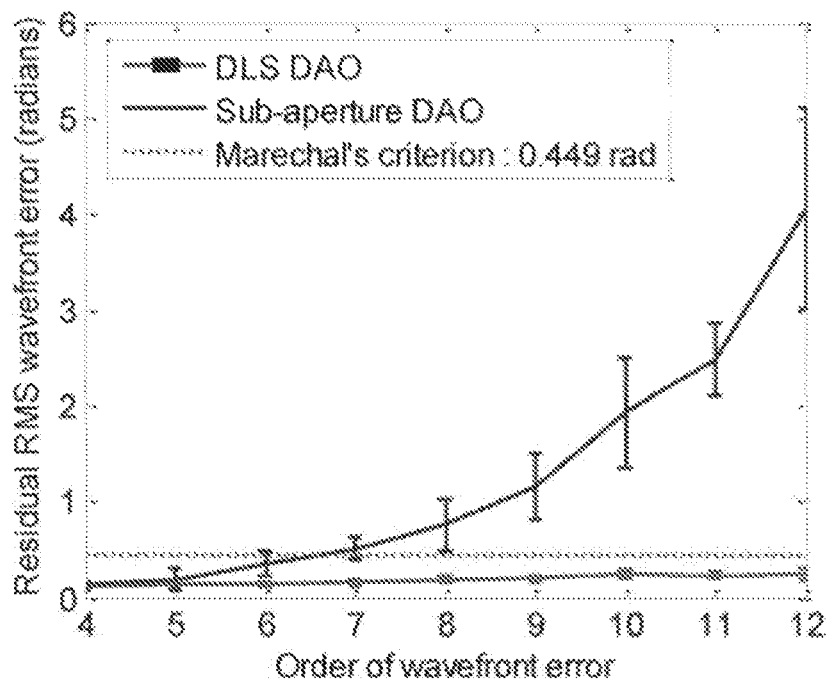
FIG. 3 shows a plot of residual RMS wave front error in radians left after correction by DLS-DAO and subaperture-DAO for increasing order of wave front error.
Figure 4:
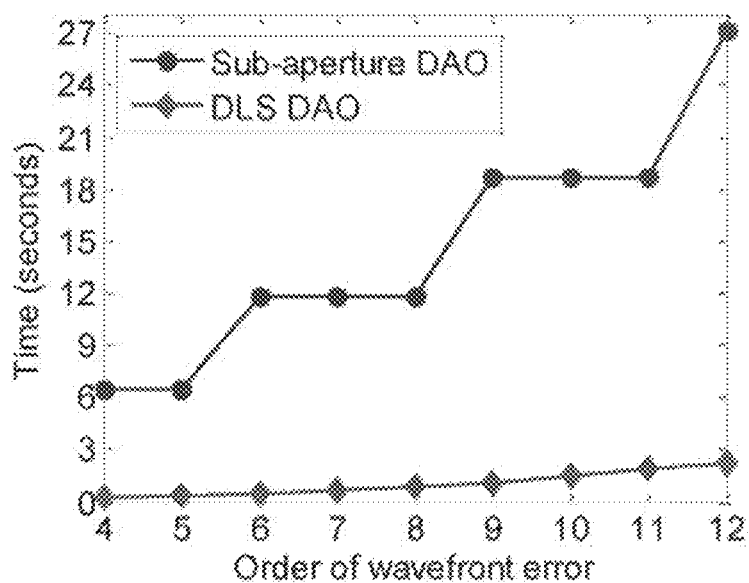
FIG. 4 is a comparison of the computation time for DLS-DAO and subaperture-DAO for increasing order of wave front error.

FIGS. 2(a), 2(g) and 2(m) show the simulated PSFs affected by $6^{th}$ order phase error with P-V error of 10, 20 and 30 radians as shown in FIGS. 2(d), 2(j) and 2(p) respectively. FIGS. 2(c), 2(i) and 2(o) ($3^{rd}$ column) show the result of applying phase correction based on DLS-DAO with corresponding residual phase error map as shown in FIGS. 2(f), 2(l) and 2(r) with calculated residual root mean square (RMS) error values of 0.125, 0.114 and 0.161 radians respectively. We can clearly see that smearing has been reduced and the points are more tightly focused in each case. Also, the residual RMS error value in each case is well within the Marechal's criterion of 0.449 radians for the diffraction limited performance. The results of DLS-DAO are compared with results of subaperture-DAO (2nd column of FIG. 2). In our simulations, for $4^{th}$-$5^{th}$ order phase error 5×5 subapertures were used, for $6^{th}$-$8^{th}$ order phase error 7×7 subapertures were used, for $9^{th}$-$11^{th}$ order phase error 9×9 subapertures were used, and for $12^{th}$ order phase error 11×11 subapertures were used for phase error estimation [3]. We can see that the smearing of the PSF in each case has been reduced after applying the subaperture-DAO correction and the result is comparable to DLS-DAO results for P-V phase error of 10 radians as shown in FIG. 2(b). However, for P-V phase error of 20 and 30 radians, we see that there is more smearing of PSF left even after subaperture -DAO correction as shown in FIGS. 2(h) and 2(n) as compared to the result of DLS based DAO shown in FIGS. 2(i) and 2(o) respectively. Also, the residual phase error in case of sub-aperture based DAO is large as shown in FIGS. 2(e), 2(k) and 2(q) with residual RMS error value of 0.2717, 0.5408 and 0.8311 radians respectively. Thus, for wave front error with higher P-V of 20 and 30 radians, the residual RMS wave front error values calculated after subaperture-DAO are above the Marechal's criterion of 0.449 radians for the diffraction limited performance. Thus, from the results of the computer simulations shown in FIG. 2, we can say that DLS-DAO has better performance than sub-aperture-DAO when wave front error has higher P-V. The superior performance of DLS-DAO especially for higher order wave front error is illustrated by the plots in FIG. 3. Residual RMS wave front error is calculated after correction of wave front error by both DLS-DAO method and subaperture-DAO method. Wave front error containing polynomial terms up to a given highest order was generated 10 times, and each time the P-V was set to 20 radians and coefficients of the wave front error (see Eq. 11), selected from normally distributed random numbers, were varied. The plots show the mean of residual RMS error, after correction by both methods, for the 10 trials and error bars show the standard deviation. In general, the residual RMS error increases with increasing order of wave front error. In case of subaperture-DAO the residual RMS error value increases from about 0.1443 radians for $4^{th}$ order to about 4.0639 radians for the $12^{th}$ order wave front error which is far from Marechal's criterion for the diffraction limited performance. However, residual RMS error for DLS-DAO method is well within the Marechal's criterion of 0.449 radians even for wave front error order of up to 12. Hence, we can say that in our simulation DLS-DAO method has yielded results comparable to diffraction limited performance. The higher accuracy of wave front error estimation using DLS-DAO method is due to the fact that the number of slope samples depends on total number of pixels within the aperture. For example, for pupil of size 256×256 pixels, we get $256^2$=65536 samples of slope data for both x and y component in case of DLS-DAO for any order of wave front error. Whereas, in case of subaperture method the number of samples of slope data is equal to the number of subapertures used. For example, for 7×7 sub-apertures, we get only $7^2$=49 samples of slope data for both x and y component. However, in terms of computational speed the DLS-DAO is faster than the subaperture-DAO as it does not involve cross correlation of images from the subapertures. The computational complexity for subaperture-DAO increases with high order aberrations as number of subapertures required for phase error estimation also increases. This is illustrated in FIG. 4. For a 512×512 pixel image array and $6^{th}$ order phase error, subaperture-DAO using 7×7 subapertures takes 11.8247 seconds on MATLAB (using CPU @ 3.30 GHz, 10 GB RAM), whereas DLS-DAO just takes 0.488 seconds. This indicates a huge improvement in computational speed by a factor of ~24× for the DLS-DAO over the subaperture-DAO for $6^{th}$ order phase error correction. Furthermore for $12^{th}$ order phase error, subaperture-DAO using 11×11 subapertures takes 27.116 seconds, whereas DLS based DAO takes 2.252 seconds. Thus, for $12^{th}$ order phase error correction, there is an improvement in computational speed for the DLS-DAO over the subaperture-DAO by a factor of ~12×, which is still a significant improvement.

Figure 5:
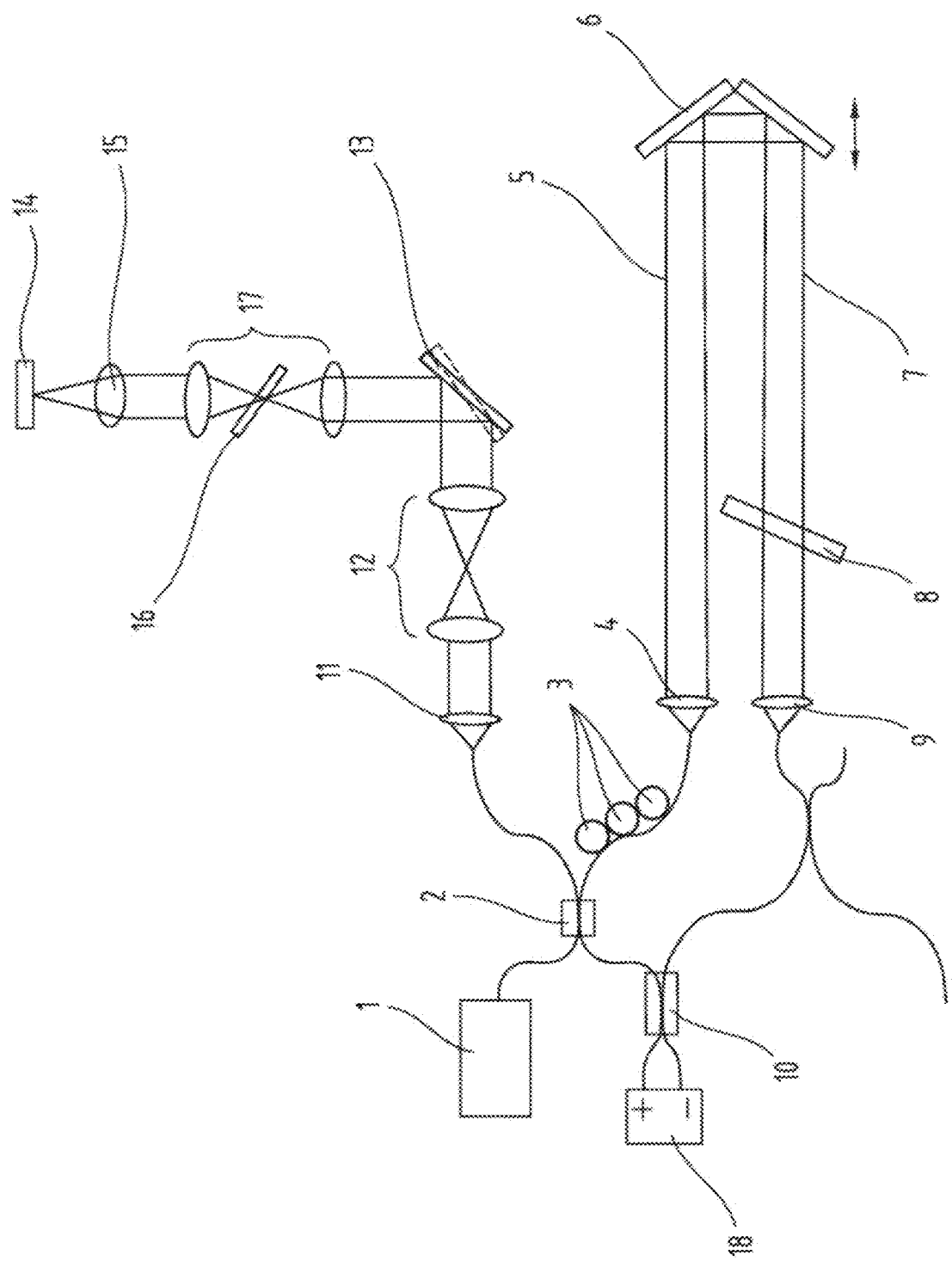
FIG. 5 shows a schematic of an embodiment of a fiber based SS OCT system according to the invention.

The experimental set-up, shown in FIG. 5, consists of a fiber based point scanning OCT system using a swept source laser 1 (AXSUN Tech., $\lambda_o$=1060 nm, $\Delta\lambda$=110 nm) with sweep rate of 100 kHz. The measured axial resolution is ~5 µm in air. The light from the laser 1 is split into the sample and the refence arm by a 50/50 fiber coupler 2. The reference arm contains some polarization paddles 3 followed by a collimating lens 4. The collimated beam 5 is reflected by the adjustable reference mirror 6. The reflected beam of light 7 is led through a neutral density filter 8 and a further collimating lens 9 before being combined with the light from the sample arm in a further fiber coupler 10. The light of the sample path, on the other hand, also passes a collimating lens 11 and a first telescope 12 before being deflected towards the sample by a X-Y galvo scanner 13. An OCT volume of size 400 (x)×400 (y)×2560 (z) is acquired using this X-Y galvo-scanner 13 (Cambridge Technology) in the sample arm. The measured sensitivity of the system is 95 dB with 1.7 mW power on the sample 14. The beam was focused on the sample 14 using a microscope objective lens 15 (Thorlabs, LSM02-BB) with the effective numerical aperture of 0.13, resulting in a lateral resolution of ~5 µm. A tilted glass plate 16 was placed at the focal plane of a second telescope 17 in the sample arm to introduce optical aberration.

The light from the sample and the reference arm is coupled and combined into the 50/50 fiber coupler 10 using the collimator lenses 9 and 11, respectively. The interference signal is detected by a dual balanced detector 18 (Thorlabs Inc., PDB430C) and digitalized at a rate of 250 M samples/s using a 12 bit analogue to digital converter (Alazartech Inc., ATS9360). A B-scan (OCT frame) rate of 250 Hz is achieved for a frame of size 400 (x)×2560 (z) pixels.

FIG. 6(a) shows the aberrated enface OCT image of the micro-beads (mean diameter ~10 µm) phantom sample acquired with the system. The micro-beads are smeared along the vertical direction due to the strong astigmatism introduced by the tilted glass plate. FIG. 6(b) shows the image obtained by applying phase correction using the sub-aperture based DAO algorithm, like in A. Kumar, W. Drexler, and R. A. Leitgeb, "Subaperture correlation based digital adaptive optics for full field optical coherence tomography," Opt. Express 21, 10850-10866 (2013). To obtain the optimal result, the method was applied in two steps: 1) defocus correction was applied to the full field of view using just two subapertures, and 2) a guide star was selected after defocus removal to estimate the higher order aberrations using 5×5 sub-apertures and up to $6^{th}$ order Zernike polynomial fitting. The guide star was selected at the location of the dotted box in FIG. 6(a). After the sub-aperture -DAO correction the image appears to be in focus and the smearing has been considerably reduced. FIG. 6(c) shows the image obtained using the DLS-DAO method. In this case only one step was required as both the defocus and higher order aberrations were estimated using the same guide star and Zernike polynomials of up to $6^{th}$ order were fitted. The image obtained by DLS-DAO (FIG. 6(c)) is more tightly focused as compared to the image obtained by subaperture-DAO (FIG. 6(b)) as the little bit of smearing left after sub-aperture-DAO correction is further reduced after DLS-DAO correction. The zoomed in view of the guide star provided in the insets in FIGS. 6(a)-(c) show the performance of the two methods. The profile plots across the guide star (normalized by the peak value of the guide star after the DLS-DAO correction) show that the profile has the smallest width after DLS correction. The full width at half maximum of the profile after subaperture-DAO correction is 12 µm, whereas after DLS-DAO correction it reduces to 8 µm. Also, the peak value of the profile after DLS-DAO correction is higher than the one after subaperture-DAO correction, indicating the higher value of signal to noise ratio (defined as $SNR=10\log_{10}$(Peak intensity pixel value/variance(Noise))). The value of the signal to noise ratio for the original image is 33 dB, whereas after the subaperture-DAO and the DLS-DAO correction it increases to 38 and 41 dB respectively. FIG. 6(d) shows the phase error estimate in radians obtained using subaperture-DAO method which contains dominant defocus and vertical astigmatism aberrations with corresponding Zernike coefficients of 0.28 and 0.33 waves respectively. Whereas, phase error estimation by DLS-DAO method, shown in FIG. 6(d), has defocus and vertical astigmatism Zernike coefficient values of 0.45 and 0.47 waves respectively. The claim that more accurate phase error estimation is done by DLS-DAO in comparison to subaperture-DAO method is supported by better image quality both in terms of resolution and signal to noise ratio enhancement. The total computational time taken by subaperture-DAO method using MATLAB was 3.2 seconds, whereas the DLS-DAO method took 0.23 seconds, which is about 14 times faster.

Figure 7:
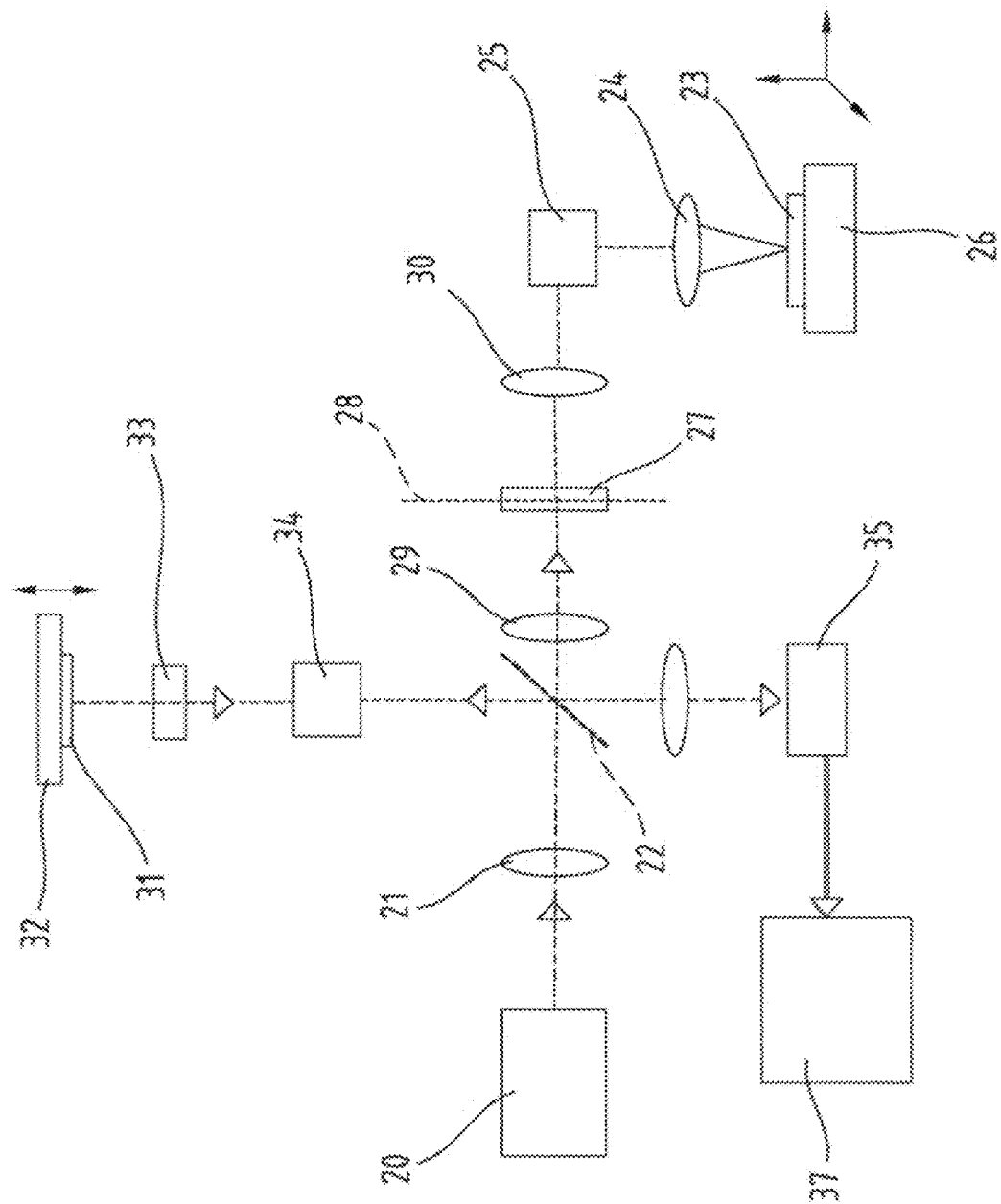
FIG. 7 is a schematic of an optical system according to the present invention, based on Michelson interferometer for a reflective sample.

FIG. 7 shows a first exemplary embodiment of an apparatus according to the present invention, in particular a schematic of the optical system based on Michelson interferometer configuration, which is suitable for reflective sample under inspection. The light source 20 used in this system can be monochromatic coherent continuous wave (CW) or pulsed laser, a frequency tuneable laser source or broad band partially coherent light source. The light from the source is collimated using collimation optics 21 which can be a combination of lenses, after which it is split into the sample arm and the reference arm using a beam-splitter 22. The light in the sample arm is focused on the sample 23 using focusing optics 24, which can be a microscope objective or combination of lenses. A two-dimensional (2-D) scanner 25 is placed at the Fourier plane of the focusing optics 24, where the beam is collimated, to scan a 2-D lateral field of view on the sample 23. The sample 23 can be placed on the three-dimensional (3-D) stage 26 to move the sample 23 laterally and also in depth. A pixelated phase mask 27 can be placed at a plane 28 conjugate to the sample plane where the beam is focused using focusing optics 29. The use of phase mask 27 is optional and can be used to produce depth encoded signal. The light is collimated back after phase mask 27 using collimation optics 30 before going to the 2-D scanner 25.

The reference arm consists of a mirror 31 on a linear translation stage 32. It also has a glass plate 33 to match the dispersion caused by the optics in the sample arm. Phase or frequency shifting device 34, which can be a moving grating or an acousto-optic modulator, in the reference arm is used to modulate interference signal in time. This is helpful for phase-shifting techniques used for extracting complex valued field information. The light reflected back from the sample 23 and from the reference mirror 31 is recombined at the beam splitter 22. The interference of light is detected by a photon-detection unit 35. The use of either imaging or collimation optics 36, placed before the detection unit 35, causes the light to be detected at either the imaging or the Fourier plane with respect to the sample plane. In case of signal detection at the Fourier plane, photo-detection unit 35 can be a 2-D array of photodetectors, which includes semiconductor based photodiode array, CCD, CMOS or InGaAs based sensors or any array of photon-sensing elements. In case of detection at the image plane, the photo-detection 35 unit can be either a 2-D array of photodetectors or a single element photodetector such a photodiode. The system can produce tomogram signal if swept source laser or tuneable frequency laser is used in combination with single element photodetector. It can also use a broad-band light source in combination of spectrometer based photon-detection unit which can consist of a diffraction grating and one-dimensional array of photo-detectors. The signal detected by the photon-detection unit 35 is sent to the processing unit 37, where it is digitalized and saved for further data processing including DLS-DAO.

Figure 8:
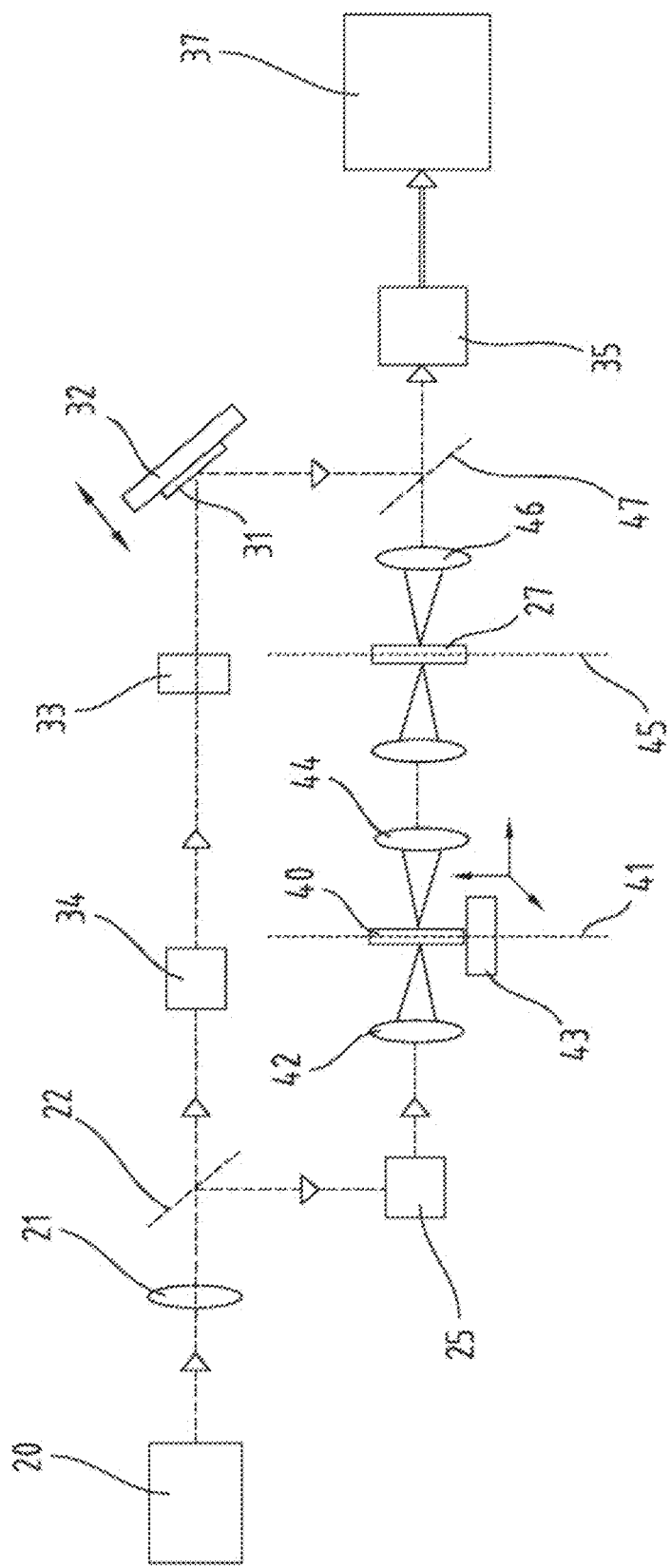
FIG. 8 shows a schematic of the optical system according to the present invention, based on a Mach Zehnder interferometer for a transmissive sample.

FIG. 8 shows a schematic of an optical system based on the Mach Zehnder interferometer configuration, which is suitable for a transmissive sample under inspection by putting into practise the principles according to the present invention. The components in the reference path, including light source 20, collimation optics 21, beam splitter 22, phase or frequency shifter 34, dispersion compensation glass 33 and adjustable mirror arrangement 31, 32 are the same as described for the system in FIG. 7. From said beam splitter 22, the sample light path branches off to at first a two-dimensional scanner 25 and is then directed onto the transmissive sample 40 in the sample plane 41 by the focusing optics 42. Said sample 40 is mounted on the three-dimensional translation stage 43. The amount of light having passed through the sample 40 is collimated by collimation optics 44 and focused onto a phase mask 27 in an intermediate image plane 45 by focusing optics 29. By means of a further collimation or imaging optics 46, the light of the sample arm is directed to pass through a second beam splitter 47, where it is combined with the light coming from the mirror 31 in the reference arm of the arrangement. The combined beams of light are then processed by the photon detection unit 35 and the processing unit 37 as explained in connection with FIG. 7.

Figure 9:
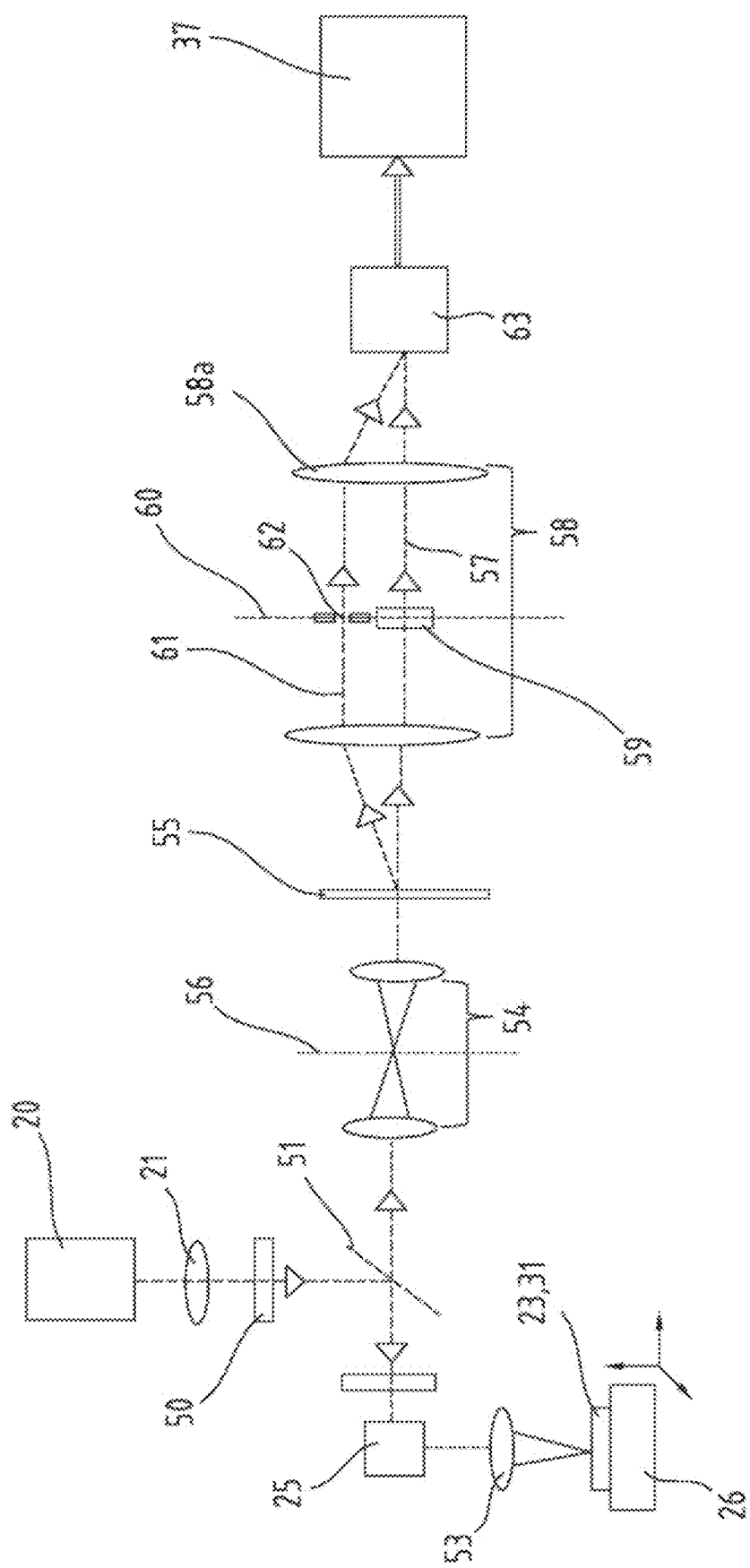
FIG. 9 is a schematic of the optical system according to the present invention, based on a common-path interferometer for both reflective and transmissive samples.

FIG. 9 shows the schematic of an embodiment of an optical system according to the present invention, based now on a common path interferometer configuration, which is suitable for both reflective and transmissive samples. The light from the source 20 is collimated by the collimation optics 21 and then additionally linearly polarized by the polarizer 50. This linearly polarized collimated beam is reflected by the polarizing beam splitter 51 and passes through the quarter wave plate 52 acting as a phase retarder to become circularly polarized. The focusing optics 53 focuses this light on either a reflective sample 23 or a mirror 31, respectively, which is placed on a 3-D translation stage 26. The reflected light after passing again through the quarter wave plate 52 becomes linearly polarized. But this time the polarization state is orthogonal to the polarization state of the input light, which is transmitted by the polarization beam splitter 51. The use of this arrangement of polarization optics is highly efficient in minimizing the optical power loss. A 2-D scanner 25 placed at the back focal plane of the focusing optics 53 can be used to scan a 2-D lateral field of view on the sample 23. The light passes through the telescope 54 and is split into two beams by the beam splitter 55 placed at the back focal plane of the telescope 54. With a mirror 31 replacing a sample 23, a transmissive object can also be placed for inspection at the intermediate focal plane 56 of the telescope 54 as shown in FIG. 9. The first beam 57 after the beam splitter 55 passes through the telescope 58 without being spatially filtered and conserves all the optical aberration it has acquired by propagating through various optics and the sample in the system. An optional pixelated phase mask 59 can be placed at the intermediate focal plane 60 where the first beam 57 is focused to produce a depth encoded signal in case the setup is used for tomography. The second beam 61 is filtered by a pin-hole 62 placed the intermediate focal plane 60 of the telescope 58. The light is then again collimated by the second lens 58a of the telescope 58. The second beam 61 becomes free of aberrations and acts as a reference beam. The interference of the first and the second beam 57, 61 is finally captured by the 2-D array 63 of photo-detectors placed at the back focal plane of the telescope 58. The detected signal is sent to the processing unit 37, where it is digitalized and saved for further data processing including DLS-DAO.

Figure 10:
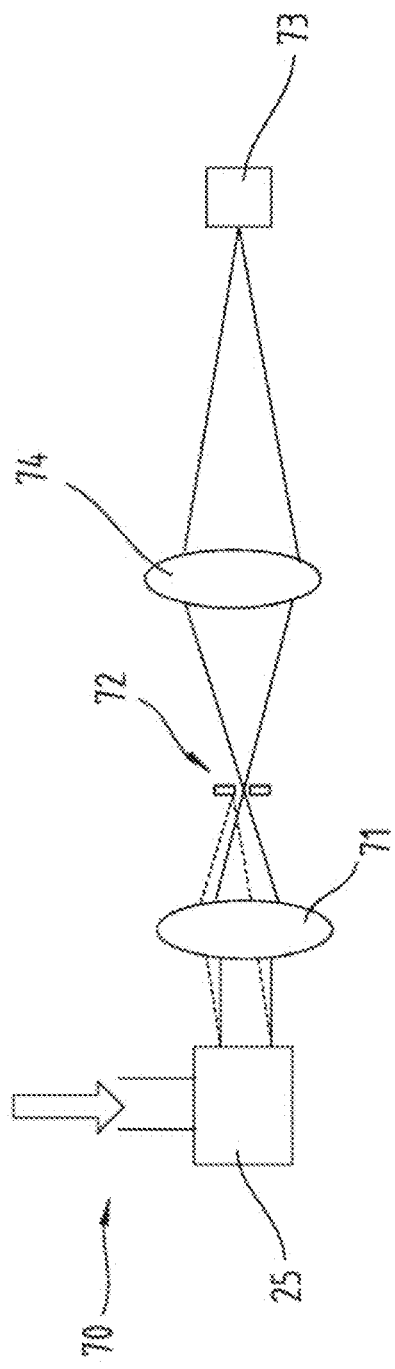
FIG. 10 shows a schematic of a photon-detection unit for use in an apparatus according to the present invention, said unit being able to laterally sample the system PSF with a single photo-detector.

In a situation where 2-D scanner 25 is at a fixed position to focus the beam on the sample at the fixed location, a photon-detection unit with an arrangement, as shown in FIG. 10, can be used to sample the system PSF. For this setup, a combined collimated reference and sample beam 70 after passing through the 2-D scanner 25 and focusing optics 71 forms a focused spot, corresponding to the system PSF, on a pinhole 72. At the pin-hole plane the spot formed by the reference beam should be bigger, free from aberration and should overlap the spot formed by the sample beam, which may contain aberration, to produce a proper interference signal. The combined overlapped spots can be translated over the pin-hole 72 with the 2-D scanner 25 placed at the focal plane of the focusing optics 71. The light passing through the pin-hole 72 for each laterally translated position is focused or imaged on to the single element photo-detector 73 by means of an imaging optics 74. This produces the 2-D lateral scan of the overlapped focused spot. Since a small angle scan is need in this case, the 2-D scanners 25 can be run at a scan speed in the range of kilo-hertz (kHz). The advantage of this arrangement is that: 1) it avoids the need for a 2-D photo-detector array which has a slower response time and lower dynamic range and 2) it can be made compatible with swept source lasers or frequency tuneable lasers that have high frequency sweep rate of above 100 kHz. When this arrangement of photon-detection unit is combined with swept source lasers can produce depth resolved PSF of the system.

Figure 11:
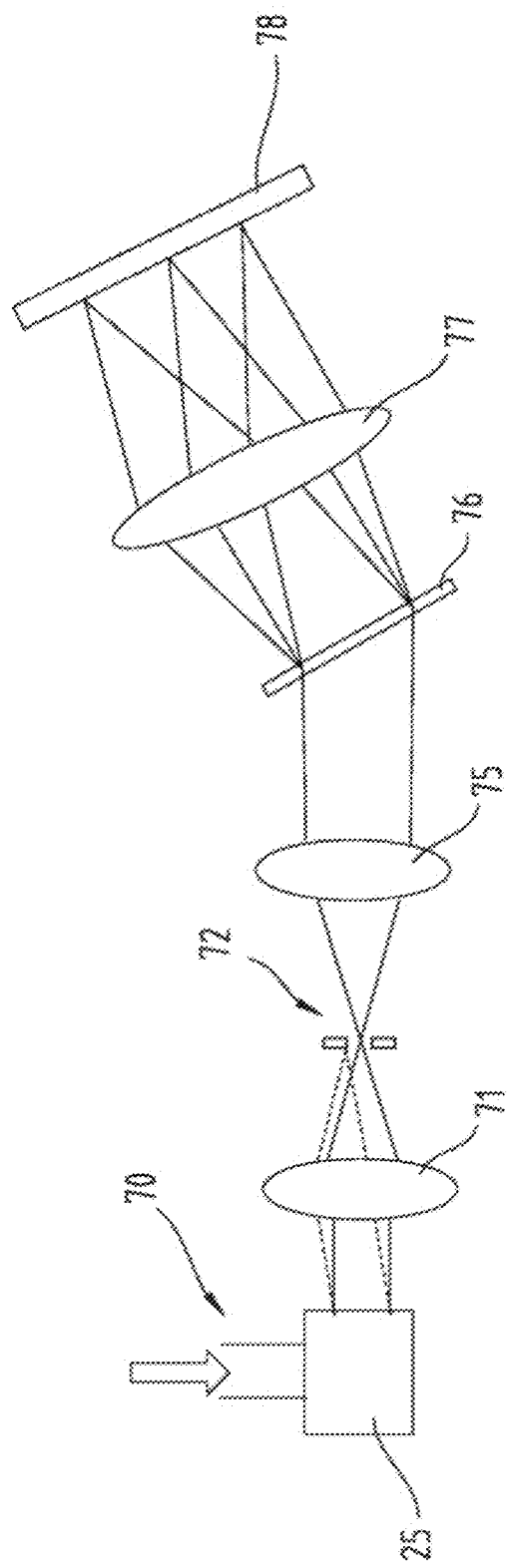
FIG. 11 is a schematic of a photon-detection unit in combination with a spectrometer for use in an apparatus according to the present invention, being able to produce a depth resolved and laterally sampled system PSF.

When used in combination with broad-band light source, the single photo-detector 73 can be replaced by a spectrometer, as shown in FIG. 11, which consists of: 1) collimation optics 75 after pin-hole 72 to collimate light, 2) diffraction grating 76 or prism to disperse light into several wavelengths, 3) focusing optics 77 to focus the dispersed light and 4) 1-D array 78 of photo-detectors to detect the focused light. This kind of setup also produces depth resolved PSF.

Figure 12:
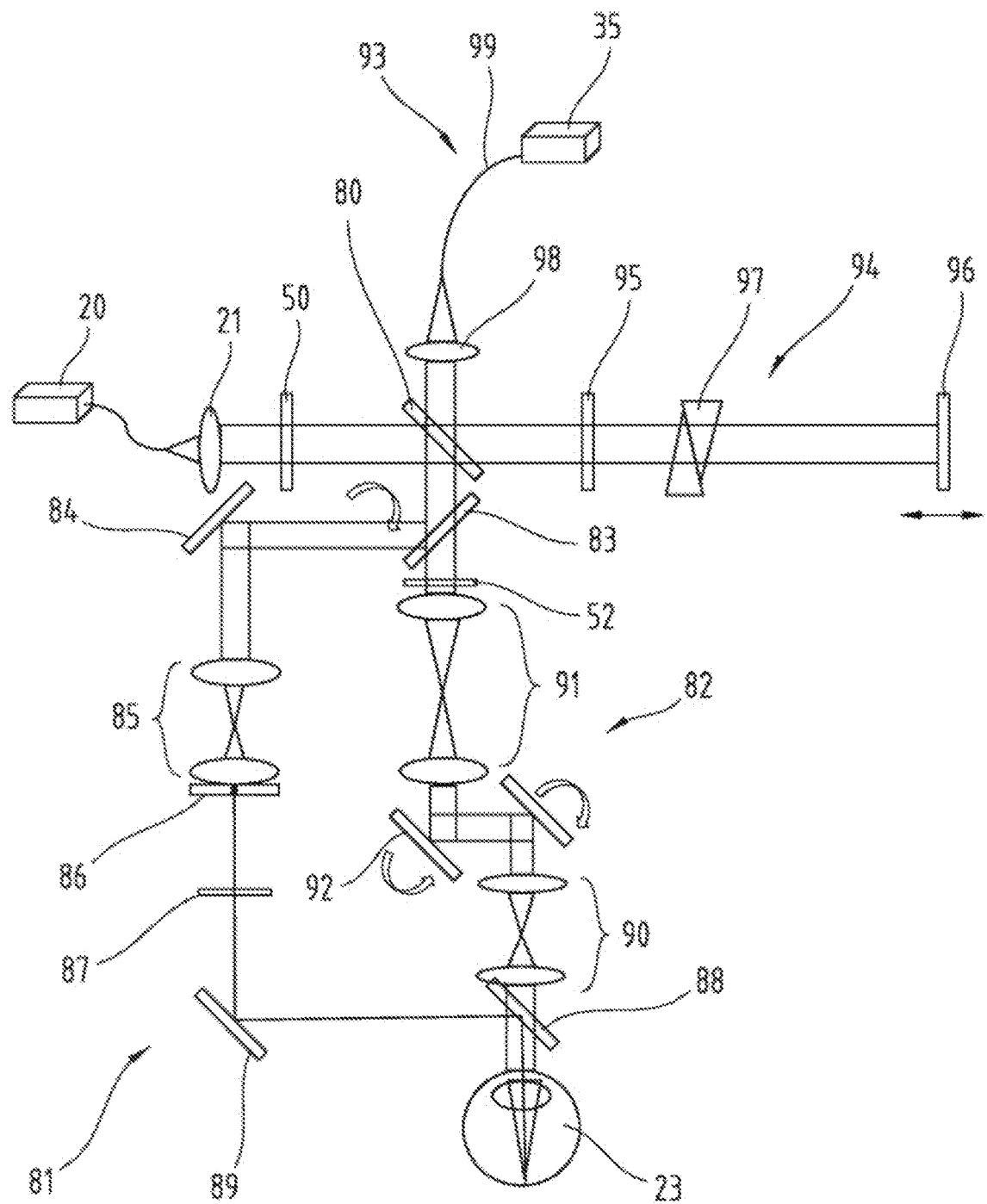
FIG. 12 is a schematic representation of an ophthalmic OCT system operating in digital aberrometry/wave front sensing mode.

FIG. 12 shows the schematic of an optical system based on OCT principle operating in the wave front sensing mode. It uses polarization optics for the optimal power management. The collimated light from a light source 20, which can be a monochromatic coherent continuous wave (CW) or pulsed laser, a frequency tuneable laser source or a broad band partially coherent light source, is s-polarized by a linear polarizer 50 after having passed a collimation lens 21 and is then split into the reference arm 94 and the sample arm 81, 82 using a non-polarizing beam-splitter 80 with a 50:50 split ratio. The sample arm is further divided into a sample illumination path 81 and a sample detection path 82—containing a quarter wave plate 52—by means of a pivotable polarizing beam splitter 83. The s-polarized light is reflected with 99% efficiency into the sample illumination path 81, containing preferably a deflection mirror 84 where the beam is reduced in diameter to less than 1 mm using a telescope 85 and an aperture 86. After passing through a quarter wave plate 87 at 45° with respect to the optical axis, the light is circularly polarized and is then diverted into a subject's eye as the reflective sample 23 using a non-polarizing beam splitter 88 with 50% power after a further deflection by mirror 89.

Due to the narrow beam diameter (<1 mm), the light does not suffer from refraction through the optics of the eye and forms a perfect diffraction limited spot on the retina. Care is taken such that the power of the focused spot on retina is less than 1 mW according to the European laser safety standard. The light that is reflected from retina passes through the full pupil of the eye and acquires the wave front aberration related to the optics of the eye, such as the lens and the cornea. 50% of the back-reflected light transmitted through non-polarizing beam splitter 88 passes through telescopes 90 and 91, with a X-Y galvo scanner system 92 arranged therebetween. The light emanating from telescope 91 passes now the polarizing beam splitter 83 and the quarter wave plate 52 as well as the first polarizing beam splitter 80. Rest of the 50% light from the eye 23 is reflected into the illumination channel and is p-polarized after passing through the quarter wave plate 87. However, most of the light is blocked from entering the detection channel 93 by the aperture 86 and the polarizing beam splitter 83, which blocks the p-polarized light with >99% efficiency. Assuming the sample 23 does not introduce any birefringence effect, the light after passing through quarter wave plate 52 is p-polarized and gets transmitted by the polarizing beam splitter 83 with ~99% efficiency. Note that the retinal nerve fiber layer (RNFL) and retinal pigment epithelium (RPE) in the eye does introduce birefringence and depolarization effect respectively. However, in case of an eye being the sample 23, optical axis of the quarter wave plates 52, 87 in the sample arm 81, 82 can be adjusted such that the major component of the back-reflected light is p-polarized. Also, the light from the reference arm 94 after passing twice through the quarter wave 95 plate is p-polarized. The reference arm 94 can optionally contain a dispersion compensation glass 97, too. The light back reflected from the sample arm 81, 82 and the reference arm 94, with its adjustable mirror 96, is combined in the non-polarizing beam splitter 80. 50% power of the interference signal after beam splitter 80 is focused using collimator 98 onto the tip of the single mode fiber 99.

Figure 13:
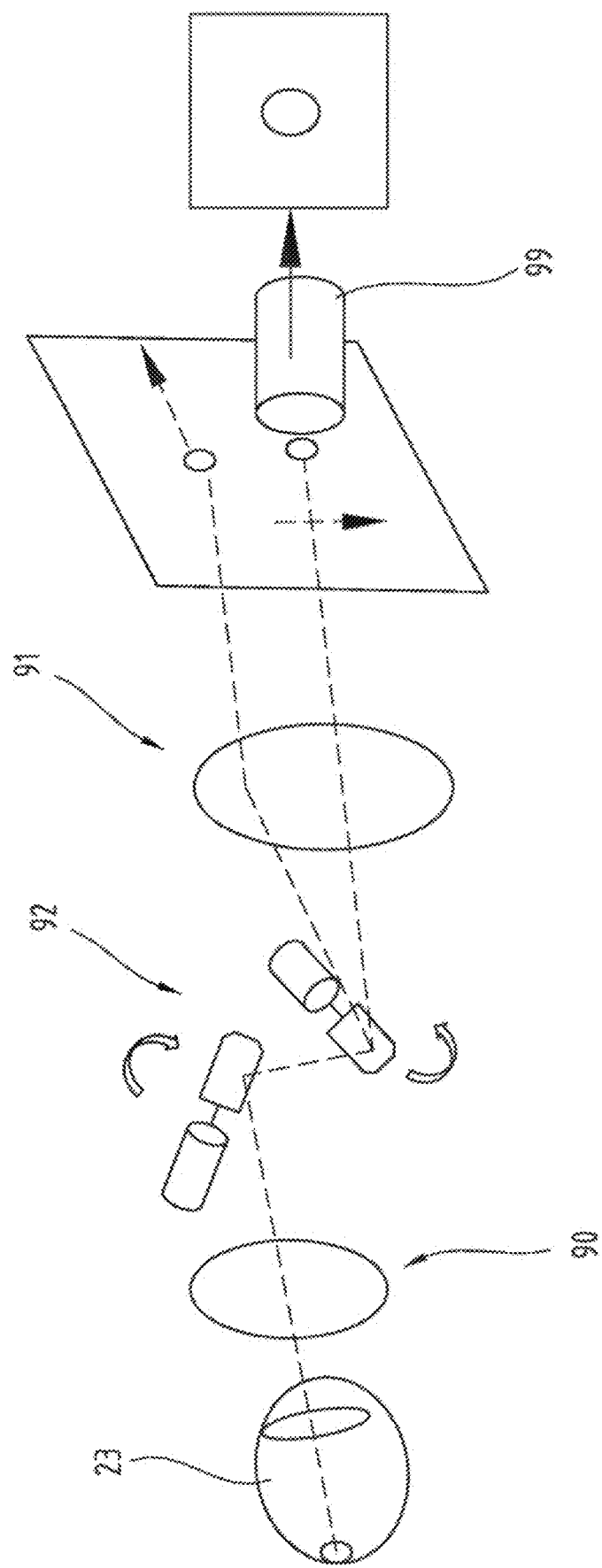
FIG. 13 is a schematic showing the concept of lateral sampling/scanning of PSF by means of galvo scanner and single mode fiber.

The image of the illumination spot on the retina, which is an approximation of the PSF of the eye 23, is sampled by laterally translating it over the tip of the single mode fiber 99 using the X-Y galvo scanner 92, as shown in FIG. 13. As the PSF is translated, the light from the area that overlaps with the mode diameter of the single mode fiber 99 is transmitted through along with the reference light, and a photon-detection unit 35 records the spectrum of the interference signal. In case of a broadband light source 20, the photon detection unit 35 is a spectrometer consisting of a diffraction grating and a line camera. In case the light source 20 is a swept source laser (SSL) or tuneable frequency laser, the photon-detection unit 35 is a single element photodetector. As the PSF is scanned, a 3-D volume OCT data is eventually recorded. After the usual OCT data processing on computer, which involves wavelength to wavenumber remapping, dispersion compensation and 1-D Fast Fourier transformation (FFT) along the spectral dimension, depth resolved PSF information corresponding to different layers in the sample 23, which in this case retina, is obtained. The PSF, corresponding to a depth layer, suffering from optical aberration is selected for processing using the digital lateral shearing (DLS)-DAO approach on computer. DLS-DAO works with point source objects, which in our case is the illumination spot generated on retina. Hence it is also quite suitable for retinal OCT where photoreceptors can act as guide star. The wave front error determined using DLS-DAO approach can be used for various clinical applications in ophthalmology such as: wave front guided refractive surgery, design of power and shape of customized intraocular and contact lenses, diagnosing keratoconus, and evaluation of vision quality after corneal and other ocular surgeries.

Figure 14:
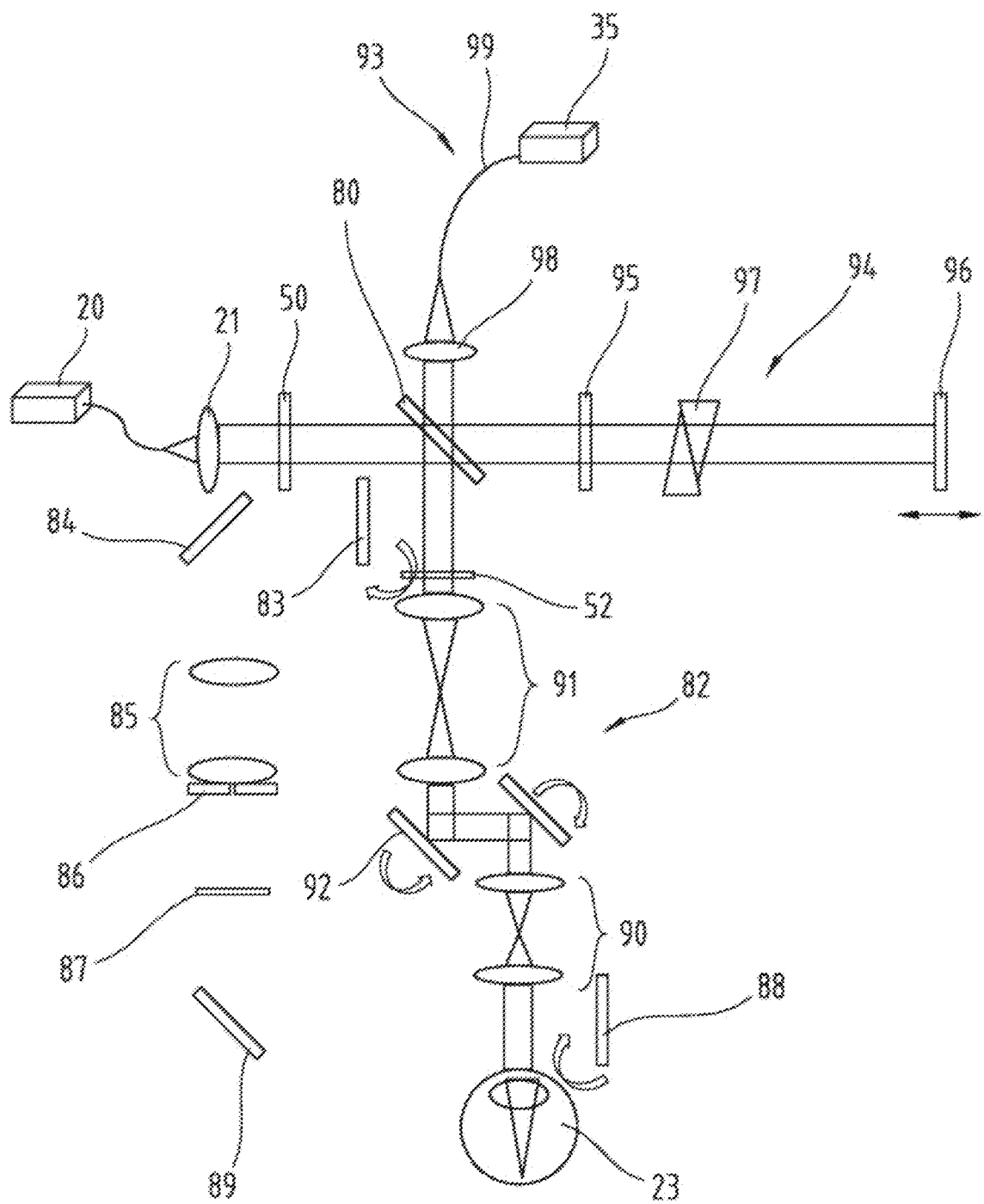

FIG. 14 shows the system operating in retinal imaging mode with some modifications. The polarizing beam splitter 83 placed near the non-polarizing beam splitter 80 close to the light source 20 and the non-polarizing beam splitter 88 placed in front of the sample/eye 23 are made pivotable and are flipped away from the path of the light beam. The system now operates as a standard OCT system. The illumination and the detection path in the sample arm is now the same. The light in the sample arm is focused on the retina and is laterally translated with the help of the X-Y galvo-scanner 92. The photon-detection unit 35 captures the interference of the light reflected by the retina, as the galvo-scanner 92 scans the lateral field of view, and the reference mirror 96. The recorded data is transferred and processed on computer to produce depth resolved volumetric image of the retinal layers. The cellular level details in 3-D, i.e. both lateral and axial dimension, can be resolved in the retinal layers if the diameter of the scanning beam at the pupil of the eye is >5 mm and the bandwidth of the light source used is >100 nm. The beam diameter of >5 mm implies a numerical aperture (NA) of >1.5. At such high numerical aperture, optical aberrations due to the optics of the eye, such as the cornea and the lens, can degrade the lateral resolution and make it difficult to resolve cellular structure such as cone-photoreceptors, which can be <5 microns in size. If OCT data is scanned at a high B-scan rate of >1.5 kHz or a corresponding volume rate of >10 Hz, then the data is phase stable with respect to the eye motion and suitable for digital aberration correction. An enface layer corresponding to photoreceptor layer in the retina can be selected for DLS-DAO method to obtain high-resolution diffraction limited images free from aberration. Note that the wave front error recorded in the wave front sensing mode as shown in FIG. 12 can also be used to correct aberration in the retinal OCT images. Thus, a combination of high resolution OCT and digital wave front sensing using DLS-DAO method can provide cellular level resolution for better visualization cone photoreceptors, retinal pigment epithelium (RPE), retinal nerve fiber layer (RNFL), retinal vessel wall and lamina cribrosa in 3-D in retina. This can help in the early diagnosis of several eye diseases such as retinal dystrophy, age related macular degeneration (AMD), glaucoma, diabetic retinopathy etc.

Figure 15:
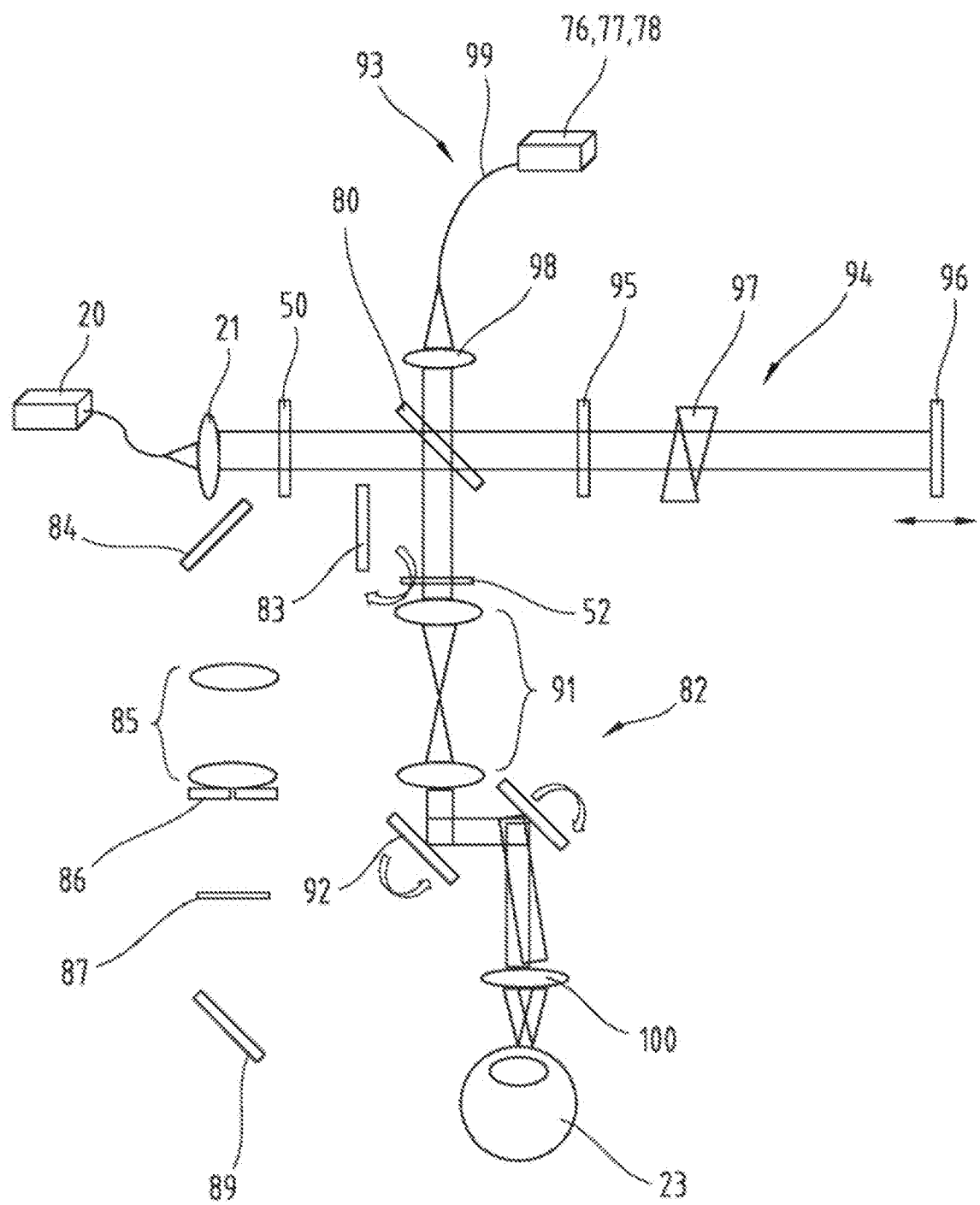
FIG. 15 is a schematic representation of the anterior segment imaging mode.

The same basic system, shown in FIGS. 12 and 14, can be used for anterior segment imaging of the human eye including the cornea, anterior chamber angle, iris and the entire crystalline lens with some modification as shown in FIG. 15. The polarizing beam splitter 83 is again flipped away from the path of the light reflected by non-polarizing beam splitter 80 placed near the light source 20 and a scan lens 100 replaces the telescope 90 in front of the subject's eye 23. The illumination and the detection path is now the same for the sample arm. The X-Y galvo scanner 92 is used to laterally scan the beam and the scan lens 100 is designed to ensure that the scan is telecentric. The light reflected from both the sample and the reference arm, after passing twice though the quarter wave plate 52, arranged at an angle of 45° to the optical axis, is mostly p-polarized and combined in the non-polarizing beam splitter 80 and coupled into the single mode fiber 99 using collimator 98. The spectrum of the interference signal is detected by a spectrometer arrangement 76, 77, 78 in the detection arm. 1-D FFT operation on the recorded signal on computer gives the depth resolved information (A-scan). A line scan using the galvo-scanner 92 across the field of view produces a cross sectional image (B-scan). High resolution corneal and anterior segment imaging is essential for pre- and post refractive surgery evaluation, glaucoma screening and intraocular lens implant planning etc. Single line scan can be made at any desired angle between 0 to 360 degrees. Dual line scans are done at angles separated by 90 degrees, say 0 to 180 degrees and 90 to 270 degrees. Quad scans are done at angles separated by 45 degrees; say 0 to 180, 45 to 225, 90 to 270, and 135 to 315 degrees, respectively. Similarly, Ns number of line scan patterns are acquired at equidistant spaced angles separated by $360/N_s$ degrees. All angles can be adjusted in increment of 1 degree with angle separation between line scans being fixed. AS OCT also provide high resolution pachymetry or corneal thickness map, which is useful for pre-surgical planning of corneal refractive surgery and early keratoconus detection. For a pachymetry map 16-line scan patterns are acquired with each line consisting of 256 A-scans, which results in 4096 measurement points. The same acquired data can be used for topographic analysis of anterior and posterior corneal surfaces. It has been shown that AS OCT is capable for providing topographic maps with high accuracy comparable to conventional corneal topography methods such as Placido disc or Scheimflug imaging, provided the scans are telecentric and calibrated for optical distortion. Topography can provide important information such as sagittal, tangential curvature maps, refractive power maps and elevation maps of both anterior and posterior corneal surface. These are useful for pre- and post corneal refractive surgery, calculation of IOL refractive power and diagnosis of irregular astigmatism following corneal transplant.

Figure 16:
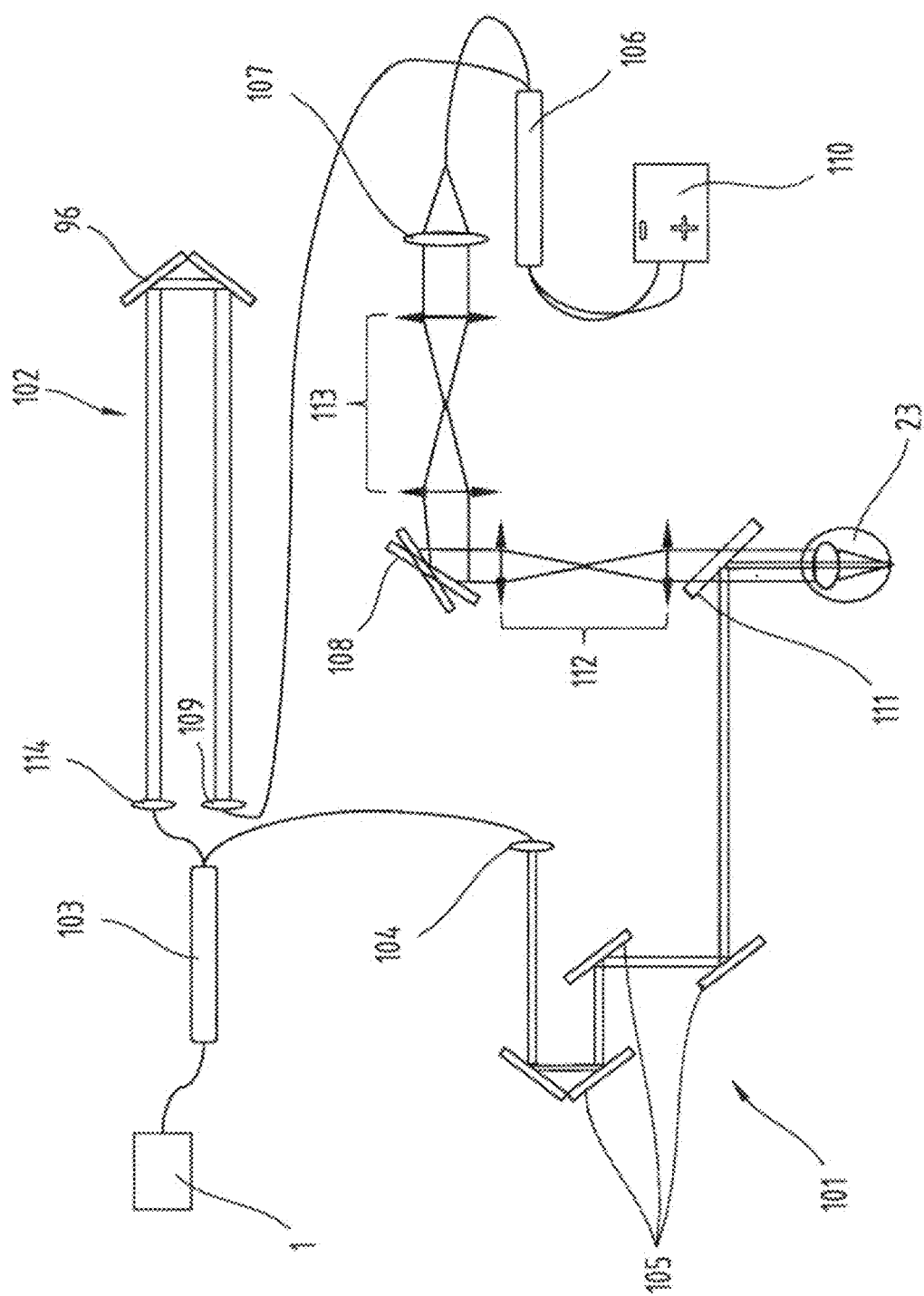
FIG. 16 shows in schematic way the experimental OCT system operating in wave front sensing mode.

FIG. 16 shows the experimental OCT setup to show the proof of principle of scanning the PSF and using DLS-DAO method to detect the wave front error. The setup consists of a fiber based interferometer with swept source laser as light source 1 with center wavelength of 1060 nm and bandwidth of 60 nm. The light from the light source 1 is split into the sample arm 101 and the reference arm 102 by a 50/50 fiber coupler 103. A narrow beam of light of diameter 2 mm that comes out of the collimator 104 of the sample arm 101 enters the sample 23 after passing through the arrangement 105 of three mirrors and being deflected by a 50/50 beam splitter 111. A phantom eye model sample 23 consisting of objective lens with focal length of 17 mm and microbeads with coverslip on top, placed at the focal plane of the objective lens, is used. The image of the focused spot on the microbeads, which represents the PSF of the system, is laterally translated over the fiber tip of one of the channel of the further 50/50 coupler 106 attached at the focal plane of the collimator 107 using the X-Y galvo scanner 108, which is interposed between two telescopes 112, 113 in similar manner as described above. This results in sampling of the PSF. The light from the sample arm 101 and the reference arm 102, containing again an adjustable reference mirror 96, is coupled and combined into said 50/50 fiber coupler 106 using the collimators 107 and 109, respectively, which is then detected by the dual balance detector 110.

Figure 17A:
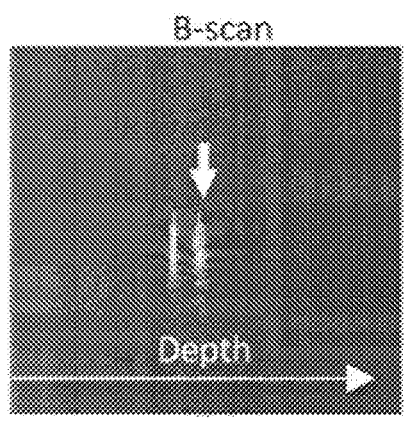
FIG. 17a is a representation of a B-scan of the recorded PSF.
Figure 17B:
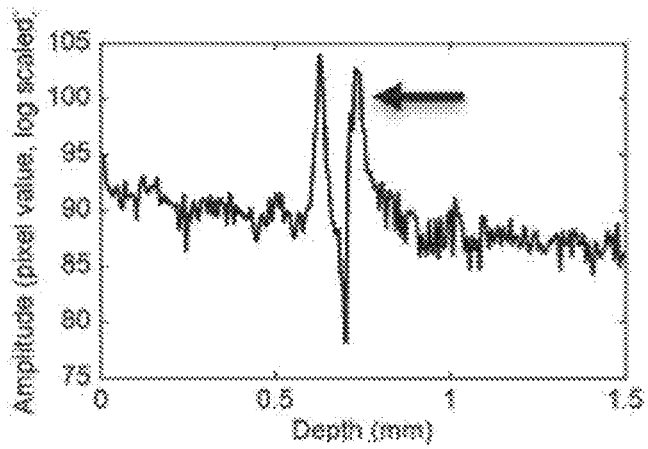
FIG. 17b shows the corresponding A-scan to FIG. 17a, FIG. 17c is a representation of the enface plane showing the scanned aberrated PSF corresponding to the micro-beads layer.
Figure 17C:
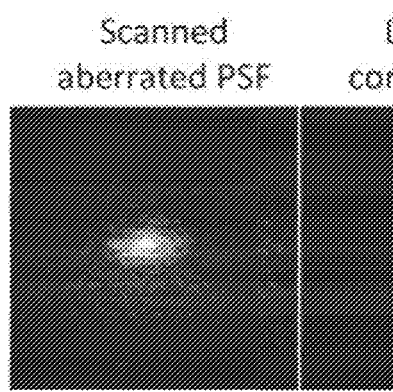
FIG. 17d shows the DLS-DAO corrected PSF.
FIG. 17e is a diagram of the estimated phase error in radians.
FIG. 17f shows profile plots of aberrated, DLS-DAO corrected and optically focused PSFs.
Figure 17D:
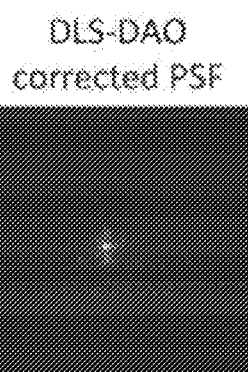
Figure 17E:
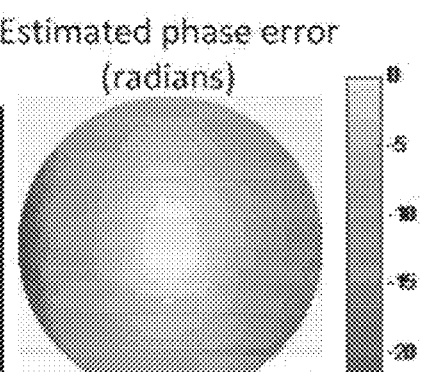
Figure 17F:
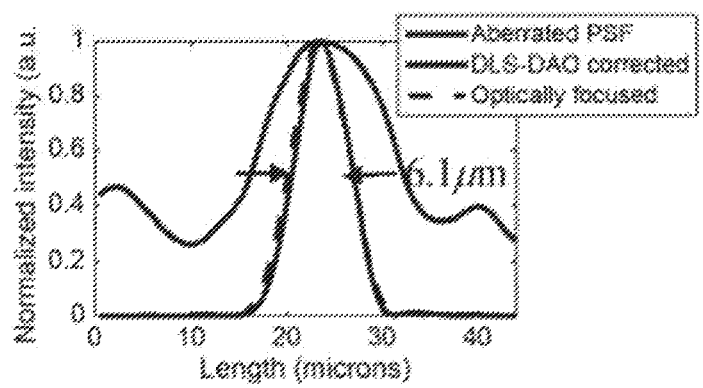

For each lateral translated position of the PSF at the tip of the fiber placed at the focal plane of collimator 107, the spectrum of interference signal (1-D data) is recorded as the laser 1 sweeps through its bandwidth. As the 2-D lateral scan of PSF is complete, a 3-D data containing volumetric information about the system PSF is generated and transferred to the computer. A simple 1-D fast Fourier transformation (FFT) along the spectral dimension yields the depth resolved PSF information. FIG. 17*a* shows the B-scan showing two depth resolved layers corresponding to glass cover slip surface and the microbeads layer, which is marked by the white arrow. FIG. 17*b* shows a corresponding A-scan, in which peak marked by arrow is from the micro-beads layer. FIG. 17*c* shows the enface image selected at the micro-beads layer which represents the scanned aberrated PSF. The aberration was introduced by displacing the micro-beads layer away from the focal plane of the objective lens. FIGS. 17*d* and 17*e* show the refocused and wave front corrected PSF and the estimated wave front error in radians using the DLS-DAO approach respectively. The PSF after wave front error correction is tightly focused. The estimated phase error shows presence of strong defocus and astigmatism aberrations with peak to valley value of 25 radians. The calculated root mean square (RMS) wave front error is 5.7 radians, which is >12 times the Marechal's criteria (RMSE=0.449 radians) for the diffraction limited performance. This implies that this method is capable of detecting strong aberrations. FIG. 17*f* shows the profile plots of aberrated, DLS-DAO corrected and optically focused PSFs for comparison. They are normalized by their respective peak values. The calculated full width at half maximum (FWHM) of the profile plot of the DLS-DAO corrected PSF is 6.2 µm, which is close to both the theoretically calculated diffraction limited spot radius of 5.7 µm and also the calculated FWHM of optically focused PSF profile of 7.1 microns. This shows that the DLS-DAO method can detect wave front error with high accuracy.

The invention claimed is:

1. An interferometric apparatus to image a point on a sample, comprising:
an optical arrangement configured to produce a sample beam and a reference beam and to produce either 1) an image of an original object field of the point at an image plane illuminated by the sample beam, the field including both amplitude information and phase information or 2) a field of the point at a pupil plane when the point is illuminated by the sample beam, the field including both amplitude information and phase information, the optical arrangement configured to produce a combination of the sample beam after illumination of the point and the reference beam;
a scanner located to receive the combination of the sample beam and reference beam and to direct the combination through focusing optics and onto a pinhole filter, the scanner and focusing optics being arranged to translate overlapping spots corresponding to the reference beam and the sample beam across the pinhole filter,
a photodetector located to receive light from the combination passing through the pinhole filter as the overlapping spots translate across the pinhole filter thereby determining a point spread function of the apparatus; and
a digital adaptive optics arrangement comprising:
(i.) a wavefront sensor configured to calculate (1) a sampled wavefront of the original object field of the point at the image plane or (2) a sampled wavefront of the object field of the point at the pupil plane, using the point spread function; and
(ii.) a computing unit adapted to:
A) generate at least one digital shifted copy of the sampled wavefront of the object at the pupil plane by
(1) using the image of the original object field of the point at the image plane to calculate the field at the pupil plane and shifting the calculated field along a horizontal or a vertical direction or an axis of a defined coordinate system of the pupil plane or
(2) using the field of the point at the pupil plane and shifting the field along a horizontal or a vertical direction or an axis of a defined coordinate system of the pupil plane and
B) determine a wavefront error in the original object field based on a phase difference between (1) a sampled wavefront of the calculated and the at least one digital shifted copy at the pupil plane or (2) the sampled wavefront of the object field of the point at the pupil plane and the at least one digital shifted copy at the pupil plane.

2. The optical apparatus according to claim 1, wherein the computing unit is adapted to generate the at least one digital shifted copy of the original object field at the pupil plane by performing, digitally, a 2-D fast Fourier transformation on the image of the original object field and then shifting the transformation of the image by at least one pixel along the horizontal direction or the vertical direction or the axis of the defined coordinate system of the pupil plane.

3. The optical apparatus according to claim 1, wherein the optical apparatus constitutes at least a portion of a digital holography system, phase sensing interferometric system or optical coherence tomography system.

4. The optical apparatus according to claim 3, further comprising:
a source of laser light or a broad band partially coherent source of light,
collimation optics for the light from the source of laser light or the broad band partially coherent source of light,
a beam splitter arrangement configured to direct a part of the light from the source of laser light or the broad band partially coherent source of light to the sample beam in a sample arm and another part of the light from the source of laser light or the broad band partially coherent source of light to the reference beam in a reference arm,
the scanner placed at a Fourier plane of the focusing optics in the sample arm,
a three-dimensional translation stage arranged as a carrier of the sample, and
the photodetector configured to detect recombined light from the sample arm and the reference arm after the beam splitter, said photodetector connected with the computing unit, the computing unit configured to digitize and process a signal corresponding to the combination of the sample beam and the reference beam to produce the phase information and amplitude information of the combination.

5. The optical apparatus according to claim 4, wherein the reference arm includes an element that matches dispersion caused by the focusing optics in the sample arm.

6. The optical apparatus according to claim 5, further comprising a phase shifting device or a frequency shifting device in the reference arm to introduce a phase shift between light in the reference arm and light in the sample arm.

7. The optical apparatus according to claim 4, further comprising a pixelated phase mask placed at a plane conjugate to the sample where the light from the source of laser light or the broad band partially coherent source of light is focused using second focusing optics and collimation optics, the second focusing optics and the collimation optics placed between the phase mask and the photodetector.

8. The optical apparatus according to claim 4, further comprising a second optical arrangement to receive light that has passed through the pinhole filter, the arrangement comprising: (1) a diffraction grating or prism, and (2) a one-dimensional array of photodetectors to receive the light from the diffraction grating or prism.

9. The optical apparatus according to claim 1, wherein the optical arrangement further comprises a light source, collimation optics and a linear polarizer for the light from the light source, a reflective polarizing beam splitter to direct the sample beam along a sample path, toward the sample,
the sample beam directed through a quarter wave plate toward the sample, a three dimensional translation stage configured to maintain the sample in the sample beam, such that the sample path after reflection from the sample includes the quarter wave plate, a first telescope arrangement, a second beam splitter located after the first telescope to separate the reference beam from the sample beam, followed by a second telescope arrangement with the pinhole filter placed at an intermediate focal plane of the first telescope for one of the beams produced by the second beam splitter, and the photodetector disposed at the back focal plane of the second telescope, said photodetector connected with the computing unit.

10. The optical apparatus according to claim 9, further comprising a pixelated phase mask placed at the intermediate focal plane of the second telescope to focus one of the beams produced by the second beam splitter, and the pinhole filter disposed to filter another of the beams produced by the second beam splitter.

11. The optical apparatus according to claim 1, wherein the optical arrangement further comprises a light source, collimation optics and a linear polarized for the light from the light source, a reflective polarizing beam splitter to direct the sample beam along a sample path,
the sample beam directed through a quarter wave plate, a mirror to reflect the sample beam, such that the sample path after reflection from the mirror includes the quarter wave plate, a first telescope arrangement, a second beam splitter located after the first telescope to separate a reference beam from the sample beam, followed by a second telescope arrangement with the pinhole filter placed at an intermediate focal plane of the first telescope for the reference beam produced by the second beam splitter and a support for placing a transmissive sample in the sample beam at the intermediate focal plane of the first telescope, and the photodetector disposed at the back focal plane of the second telescope, said photodetector connected with the computing unit.

12. The optical apparatus according to claim 1, further comprising a swept source laser or a tunable frequency laser to produce light for the sample beam and the reference beam, and wherein the photodetector comprises a single element photodetector.

13. The optical apparatus according to claim 1, further comprising a broad-band light source to produce light for the sample beam and the reference beam and wherein the photodetector comprises a spectrometer.

14. The optical apparatus according to claim 1, further comprising a light source including a monochromatic coherent continuous wave (CW) or pulsed laser, a frequency tuneable laser source or a broad band partially coherent light source to produce the sample beam and the reference beam, the light source followed by a linear polarizer and a non-polarizing beam-splitter arranged to receive light from the light source,
the path of the sample beam containing a first telescope and an aperture, a first quarter wave plate at 45° with respect to an optical axis of the sample beam, and a non-polarizing beam splitter, and
the path for light after illumination of the point containing the non-polarizing beam splitter, a second and third telescopes with an X-Y galvo scanner system intermediate the second and third telescopes, and the first quarter wave plate, and
the reference path containing an adjustable reference mirror, a second quarter wave plate and a dispersion compensation glass.

15. The optical apparatus according to claim 14, further comprising a polarizing beam splitter disposed between the non-polarizing beam splitter and the second telescope of the sample path, said polarizing beam splitter or the non-polarizing beam splitter placed before the sample, the polarizing beam splitting of the sample path of the non-polarizing beam splitter of the sample path being pivotable in and out of the path of the sample beam.

16. The optical apparatus according to claim 1, further comprising a swept source laser as a light source, a fiber coupler branching to direct light from the light source into the sample beam in a sample light path and to direct light into the reference beam in a reference light path, the reference light path containing a collimator, an adjustable reference mirror and a second collimator, the sample light path containing a third collimator, at least one deflection mirror and a beam splitter,
the apparatus further comprising a telescope disposed to receive light from the beam splitter after the light traverses the sample location, followed by a X-Y galvo scanner, a second telescope and a fourth collimator, the light in the sample path and the light in the reference light path aligned to combine together into a second fiber coupler, the output side of the second fiber coupler connected to a dual balance detector.

17. The optical apparatus according to claim 1, wherein the pinhole filter comprises a pinhole aperture or a tip of a single mode fiber.

18. A non-transitory computer readable medium having executable programming instructions stored thereon comprising program code for:
generating at least one laterally translated digital copy of an original object field of an optical apparatus at a spatial Fourier plane along the horizontal or vertical direction or axis of a defined coordinate system of the pupil plane; and determining a wavefront error based on a phase difference between an original wavefront and a digital copy or copies of the original wavefront.

19. The non-transitory computer readable medium having executable programming instructions stored thereon according to claim 18, wherein the code is adapted to generate the translated digital copy of the original object field as an original object field at the pupil plane, by performing digitally a 2-D fast Fourier transformation on an image field and then shifting the original object field by at least one pixel along the horizontal or vertical direction or axis of a defined coordinate system of the spatial Fourier or pupil plane.

20. The non-transitory computer readable medium having executable programming instructions stored thereon according to claim 18, wherein the step of determining the wavefront comprises multiplying pixel-by-pixel the original wavefront with a complex conjugate of the translated digital copy and calculating slope per pixel of the wavefront error.

* * * * *

UNITED STATES PATENT AND TRADEMARK OFFICE
CERTIFICATE OF CORRECTION

| | | |
|---|---|---|
| PATENT NO. | : 11,896,303 B2 | Page 1 of 1 |
| APPLICATION NO. | : 16/630217 | |
| DATED | : February 13, 2024 | |
| INVENTOR(S) | : Abhishek Kumar | |

It is certified that error appears in the above-identified patent and that said Letters Patent is hereby corrected as shown below:

In the Claims

Column 22, Lines 27-28 should read:
"sampled wavefront of the calculated original object field at the pupil plane and the at least one digital shifted copy at the pupil plane or"

Column 23, Line 53 should read:
"collimation optics and a linear polarizer for the light from"

Column 24, Line 40 should read:
"izing beam splitter of the sample path or the non-polarizing"

Signed and Sealed this
Twenty-sixth Day of November, 2024

Katherine Kelly Vidal
*Director of the United States Patent and Trademark Office*